US008435952B2

(12) United States Patent
Vratsanos et al.

(10) Patent No.: US 8,435,952 B2
(45) Date of Patent: *May 7, 2013

(54) METHOD FOR RETARDING PROGRESSION TO DEFINITE RHEUMATOID ARTHRITIS IN SUBJECTS WITH UNDIFFERENTIATED ARTHRITIS

(76) Inventors: George Vratsanos, Yardley, PA (US); Jean-Claude Becker, Princeton, NJ (US); Michael Corbo, Flemington, NJ (US)

( * ) Notice: Subject to any disclaimer, the term of this patent is extended or adjusted under 35 U.S.C. 154(b) by 164 days.

This patent is subject to a terminal disclaimer.

(21) Appl. No.: 13/024,601

(22) Filed: Feb. 10, 2011

(65) Prior Publication Data

US 2011/0142835 A1    Jun. 16, 2011

Related U.S. Application Data

(63) Continuation of application No. 12/387,359, filed on May 1, 2009, now Pat. No. 7,915, 222.

(60) Provisional application No. 61/050,336, filed on May 5, 2008.

(51) Int. Cl.
*A61K 38/17* (2006.01)
*A61K 39/395* (2006.01)

(52) U.S. Cl.
USPC ...................... 514/21.2; 424/134.1

(58) Field of Classification Search .................. None
See application file for complete search history.

(56) References Cited

U.S. PATENT DOCUMENTS

| | | | |
|---|---|---|---|
| 5,434,131 A | 7/1995 | Brady et al. | |
| 5,521,288 A | 5/1996 | Brady et al. | |
| 5,580,756 A | 12/1996 | Brady et al. | |
| 5,770,197 A | 6/1998 | Brady et al. | |
| 5,773,253 A | 6/1998 | Ledbetter et al. | |
| 5,844,095 A | 12/1998 | Brady et al. | |
| 5,851,795 A | 12/1998 | Brady et al. | |
| 5,885,579 A | 3/1999 | Brady et al. | |
| 5,885,796 A | 3/1999 | Brady et al. | |
| 5,916,560 A | 6/1999 | Aruffo et al. | |
| 5,968,510 A | 10/1999 | Brady et al. | |
| 5,977,318 A | 11/1999 | Brady et al. | |
| 6,090,914 A | 7/2000 | Brady et al. | |
| 6,641,809 B1 | 11/2003 | Brady et al. | |
| 6,830,937 B1 | 12/2004 | Brady et al. | |
| 7,094,874 B2 | 8/2006 | Peach et al. | |
| 7,304,033 B2 | 12/2007 | Larsen et al. | |
| 7,307,064 B2 | 12/2007 | Rusnak | |
| 7,332,303 B2 | 2/2008 | Schilling et al. | |
| 7,455,835 B2 | 11/2008 | Cohen et al. | |
| 7,528,111 B2 | 5/2009 | Vratsanos et al. | |
| 7,541,164 B2 | 6/2009 | Schilling et al. | |
| 7,915,222 B2 * | 3/2011 | Vratsanos et al. | 514/16.6 |
| 2002/0031510 A1 | 3/2002 | Larsen et al. | |
| 2002/0039577 A1 | 4/2002 | Todderud et al. | |
| 2003/0007968 A1 | 1/2003 | Adams et al. | |
| 2003/0219863 A1 | 11/2003 | Peach et al. | |
| 2004/0014171 A1 | 1/2004 | Peach et al. | |
| 2004/0022787 A1 | 2/2004 | Cohen et al. | |
| 2005/0196402 A1 | 9/2005 | Gray et al. | |

FOREIGN PATENT DOCUMENTS

| | | |
|---|---|---|
| WO | WO2007/076032 | 7/2007 |
| WO | WO2007/076354 | 7/2007 |

OTHER PUBLICATIONS

American Thoracic Society, "Diagnostic Standards and Classification of Tuberculosis in Adults and Children", Am J Respir Crit Care Med., vol. 161, pp. 1376-1395 (2000).
American Thoracic Society, "Targeted Tuberculin Testing and Treatment of Latent Tuberculosis Infection", Am J Respir Crit Care Med., vol. 161, pp. S221-S247 (2000).
Balsa, A. et al., "Differential Expression of the Costimulatory Molecules B7.1(CD80) and B7.2 (CD86) in Rheumatoid Synovial Tissue", British Journal of Rheumatology, vol. 35, pp. 33-37 (1996).
Birrell, F.N. et al., "How does the Short Form 36 Health Questionnaire (SF-36) in Rheumatoid Arthritis (RA) Relate to RA Outcome Measures and SF-36 Population Values? A Cross-Sectional Study", Clin Rheumatol, vol. 19, pp. 195-199 (2000).
Broach, J., "Construction of High Copy Yeast Vectors Using 2-µm Circle Sequences", Methods in Enzymology, vol. 101, pp. 307-325 (1983).
Clarke, L. et al., "Selection Procedure for Isolation of Centromere DNAs from *Saccharomyces cerevisiae*", Methods in Enzymology, vol. 101, pp. 300-306 (1983).
Cohen, S. et al., "Nonchromosomal Antibiotic Resistance in Bacteria: Genetic Transformation of *Escherichia coil* by R-Factor DNA", PNAS, vol. 69(8), pp. 2110-2114 (1972).
Cush, J. et al., "Phenotypic Analysis of Synovial Tissue and Peripheral Blood Lymphocytes Isolated from Patients with Rheumatoid Arthritis", Arthritis and Rheumatism, vol. 31(10), pp. 1230-1238 (1988).
Emery, P., "The Optimal Management of Early Rheumatoid Disease: The Key to Preventing Disability", British Journal of Rheumatology, vol. 33, pp. 765-768 (1994).
Felson, D. et al., "The American College of Rheumatology Preliminary Core Set of Disease Activity Measures for Rheumatoid Arthritis Clinical Trials", Arthritis and Rheumatism, vol. 36(6), pp. 729-740 (1993).
Fiers, W. et al., "Complete nucleotide sequence of SV40 DNA", Nature, vol. 273, pp. 113-120 (1978).
Firestein, G. et al., "Quantitative Analysis of Cytokine Gene Expression in Rheumatoid Arthritis", The J. of Immunology, vol. 144, pp. 3347-3353 (1990).
Firestein, G et al., "How Important are T Cells in Chronic Rheumatoid Synovitis?", Arthritis and Rheumatism, vol. 33(6), pp. 768-773 (1990).
Førre, Ø. et al., "Augmented Numbers of HLA-DR-Positive T Lymphocytes in the Synovial Fluid and Synovial Tissue of Patients with Rheumatoid Arthritis and Juvenile Rheumatoid Arthritis", Scand. J. Immunol., vol. 15, pp. 227-231 (1982).

(Continued)

*Primary Examiner* — Ilia Ouspenski
(74) *Attorney, Agent, or Firm* — Nickki Parlet

(57) ABSTRACT

The invention relates to methods and compositions for treating undifferentiated arthritis (UA) and/or preventing the development of rheumatoid arthritis (RA) in subjects with UA by administering to a subject in need thereof an effective amount of soluble CTLA4 molecule.

12 Claims, 3 Drawing Sheets

OTHER PUBLICATIONS

Fries, J. et al., "Measurement of Patient Outcome in Arthritis", Arthritis & Rheumatism, vol. 23(2), pp. 137-145 (1980).

Fries, J. et al., "The Dimensions of Health Outcomes: The Health Assessment Questionnaire, Disability & Pain Scales", The J. of Rheumatology, vol. 9(5), pp. 789-793 (1982).

Furst, D E. et al., "Preliminary guidelines for diagnosing and treating tuberculosis in patients with rheumatoid arthritis in immunosuppressive trials or being treated with biological agents", Ann Rheum Dis., vol. 61, pp. 62-63 (2002).

Goeddel, D. et al., "Synthesis of human fibroblast interferon by *E. coli*", Nucleic Acids Research, vol. 8(18), pp. 4057-4074 (1980).

Harrison, B.J. et al., "Natural Remission in Inflammatory Polyarthritis: Issues of Definition and Prediction", British J of Rheumatology, vol. 35, pp. 1096-1100 (1996).

Hess, B. et al., "Cooperation of Glycolytic Enzymes", J. Adv. Enzyme Reg., vol. 7, pp. 149-167 (1968).

Hitzeman, R. et al., "Isolation and Characterization of the Yeast 3-Phosphoglycerokinase Gene (PGK) by an Immunological Screening Technique", The J. of Biological Chemistry, vol. 255(2), pp. 12073-12080 (1980).

Hochberg,M. et al., "Epidemiology of Rheumatoid Arthritis: Update", Epidemiologic Reviews, vol. 12, pp. 247-252 (1990).

Holland, M. et al., "Isolation and identification of yeast messenger ribonucleic acids coding for enolase, glyceraldehyde-3-phosphate dehydrogenase, and phosphoglycerate kinase", Biochemistry, vol. 17(23), pp. 4900-4907 (1978).

Karin, M. et al., "Human metallothionein genes-primary structure of the metallothionein-II gene and a related processed gene", Nature, vol. 299, pp. 797-802 (1982).

Keller, S. et al., "The SF-36 Arthritis-Specific Health Index (ASHI)", Medical Care, vol. 37(5), pp. MS51-MS60 Supplement (1999).

Kidd, B L. et al., "Immunohistological features of synovitis in ankylosing spondylitis: a comparison with rheumatoid arthritis", Ann Rheum Dis., vol. 48, pp. 92-98 (1989).

Klareskog, L. et al., "Relationships between HLA-DR-expressing Cells and T Lymphocytes of Different Subsets in Rheumatoid Synovial Tissue", Scand. J. Immunol., vol. 15, pp. 501-507 (1982).

Kolhekar, A. et al., "Peptidylglycine-Hydroxylating Monooxygenase: Active Site Residues, Disulfide Linkages, and a Two-Domain Model of the Catalytic Core", Biochemistry, vol. 36(36), pp. 10901-10909 (1997).

Konttinen, Y. et al., "Characterization of the Immunocompetent Cells of Rheumatoid Synovium from Tissue Sections and Eluates", Arthritis & Rheumatism, vol. 24(1), pp. 71-79 (1981).

Kosinski, M. et al., "The SF-36 Health Survey as a Generic Outcome Measure in Clinical Trials of Patients with Osteoarthritis and Rheumatoid Arthritis", Medical Care, vol. 37(5), pp. MS23-MS39 Supplement (1999).

Laffon, A. et al., "Upregulated Expression and Function of VLA-4 Fibronectin Receptors on Human Activated T Cells in Rheumatoid Arthritis", J. Clin. Invest., vol. 88, pp. 546-552 (1991).

Liu, M. et al., "The Presence of Costimulatory Molecules CD86 and CD28 in Rheumatoid Arthritis Synovium", Arthritis & Rheumatism, vol. 39(1), pp. 110-114 (1996).

Markenson, J.A., "Worldwide Trends in the Socioeconomic Impact and Long-Term Prognosis of Rheumatoid Arthritis", Seminars in Arthritis and Rheumatism, vol. 21(2), pp. 4-12 (1991).

McGonagle, D. et al., "The Relationship between Synovitis and Bone Changes in Early Untreated Rheumatoid Arthritis", Arthritis & Rheumatism, vol. 42(8), pp. 1706-1711 (1999).

Østergaard, M. et al., "OMERACT Rheumatoid Arthritis Magnetic Resonance Imaging Studies. Core Set of MRI Acquisitions, Joint Pathology Definitions, and the OMERACT RA-MRI Scoring System", J Rheumatol, vol. 30, pp. 1385-1386 (2003).

Ranheim, E. et al., "Elevated Expression of CD80 (B7/BB1) and other Accessory Molecules on Synovial Fluid Mononuclear Cell Subsets in Rheumatoid Arthritis", Arthritis & Rheumatism, vol. 37(11), pp. 1637-1646 (1994).

Redlich, K. et al., "Rheumatoid Arthritis Therapy After Tumor Necrosis Factor and Interleukin-1 Blockade", Arthritis & Rheumatism, vol. 48(12), pp. 3308-3319 (2003).

Saleem, B. et al., "Does a New Threshold of DAS 28 Predict Imaging Assessed Remission in RA?", Ann Rheum Dis, vol. 66(Suppl ll):186 (2007).

Sambrook, J., Molecular Cloning, A Laboratory Manual, Cold Spring Harbor Laboratory Press (1989).

Sfikakis, P. et al., "Expression of CD28, CTLA4, CD80, and CD86 Molecules in Patients with Autoimmune Rheumatic Diseases: Implications for Immunotherapy", Clinical Immunology and Immunopathology, vol. 83(3), pp. 195-198 (1997).

Shimatake, H. et al., "Purified λ regulatory protein cII positively activates promoters for lysogenic development", Nature, vol. 292, pp. 128-132 (1981).

Spector, T., "Rheumatoid Arthritis", Rheumatic Disease Clinics of North America, vol. 16(3), pp. 513-537 (1990).

Stinchcomb, D. et al., "Isolation and characterisation of a yeast chromosomal replicator", Nature, vol. 282, pp. 39-43 (1979).

Thomas, R. et al., "Functional Differentiation of Dendritic Cells in Rheumatoid Arthritis", The J. of Immunology, vol. 156, pp. 3074-3086 (1996).

Toyama, R. et al., "Human chorionic gonadotropin α and human cytomegalovirus promoters are extremely active in the fission yeast *Schizosaccharomyces pombe*", FEBS, vol. 268(1), pp. 217-221 (1990).

Tschumper, G. et al., "Sequence of a yeast DNA fragment containing a chromosomal replicator and the *TRP1* gene", Gene, vol. 10, pp. 157-166 (1980).

Urlaub, G. et al., "Effect of Gamma Rays at the Dihydrofolate Reductase Locus: Deletions and Inversions", Somatic Cell and Molecular Genetics, vol. 12(6), pp. 555-566 (1986).

Van Boxel, J. et al., "Predominantly T-Cell Infiltrate in Rheumatoid Synovial Membranes", The New England Journal of Medicine, vol. 293(11), pp. 517-520 (1975).

Van der Merwe, P. Anton et al., "CD80 (B7-1) Binds Both CD28 and CTLA-4 with a Low Affinity and Very Fast Kinetics", J. Exp. Med., vol. 185(3), pp. 393-403 (1997).

Van Gaalen, F. et al., "Autoantibodies to Cyclic Citrullinated Peptides Predict Progression to Rheumatoid Arthritis in Patients with Undifferentiated Arthritis", Arthritis & Rheumatism, vol. 50(3), pp. 709-715 (2004).

Wakefield, R. et al., "The Value of Sonography in the Detection of Bone Erosions in Patients with Rheumatoid Arthritis", Arthritis & Rheumatism, vol. 43(12), pp. 2762-2770 (2000).

Ware, Jr. John et al., The SF-36 Arthritis-Specific Health Index (ASHI) Medical Care, vol. 37(5), pp. MS40-MS50 (1999).

Wolfe, Frederick, "The epidemiology of drug treatment failure in rheumatoid arthritis", Bailliere's Clinical Rheumatology, vol. 9(4), pp. 619-632 (1995).

Zvaifler, N. et al., "Pannus and Pannocytes Alternative Models of Joint Destruction in Rheumatoid Arthritis", Arthritis & Rheumatism, vol. 37(6), pp. 783-789 (1994).

Haque, U. et al., "The role of biologicals in early rheumatoid arthritis", Best Practice & Research Clinical Rheumatology, vol. 19(1), pp. 179-189 (2005).

van der Helm-van Mil, A. et al., "A prediction rule for disease outcome in patients with recent-onset undifferentiated arthritis: how to guide individual treatment decisions", Arthritis & Rheumatism, vol. 56(2) pp. 433-440 (2007).

* cited by examiner

FIG. 1

```
1   AGCTTCACCA ATG GGT GTA CTG CTC ACA CAG AGG ACG CTG
               M   G   V   L   L   T   Q   R   T   L
               → Oncostatin M Signal Sequence →
41  CTC AGT CTG GTC CTT GCA CTC CTG TTT CCA AGC ATG GCG
    L   S   L   V   L   A   L   L   F   P   S   M   A
80  AGC ATG GCA ATG CAC GTG GCC CAG CCT GCT GTG GTA CTG
    S   M   A   M   H   V   A   Q   P   A   V   V   L
               → Human CTLA4 →
119 GCC AGC AGC CGA GGC ATC GCC AGC TTT GTG TGT GAG TAT
    A   S   S   R   G   I   A   S   F   V   C   E   Y
158 GCA TCT CCA GGC AAA GCC ACT GAG GTC CGG GTG ACA GTG
    A   S   P   G   K   A   T   E   V   R   V   T   V
197 CTT CGG CAG GCT GAC AGC CAG GTG ACT GAA GTC TGT GCG
    L   R   Q   A   D   S   Q   V   T   E   V   C   A
236 GCA ACC TAC ATG ATG GGG AAT GAG TTG ACC TTC CTA GAT
    A   T   Y   M   M   G   N   E   L   T   F   L   D
275 GAT TCC ATC TGC ACG GGC ACC TCC AGT GGA AAT CAA GTG
    D   S   I   C   T   G   T   S   S   G   N   Q   V
314 AAC CTC ACT ATC CAA GGA CTG AGG GCC ATG GAC ACG GGA
    N   L   T   I   Q   G   L   R   A   M   D   T   G
353 CTC TAC ATC TGC AAG GTG GAG CTC ATG TAC CCA CCG CCA
    L   Y   I   C   K   V   E   L   M   Y   P   P   P
392 TAC TAC CTG GGC ATA GGC AAC GGA ACC CAG ATT TAT GTA
    Y   Y   L   G   I   G   N   G   T   Q   I   Y   V
431 ATT GAT CCA GAA CCG TGC CCA GAT TCT GAT CAG GAG CCC
    I   D   P   E   P   C   P   D   S   D   Q   E   P
470 AAA TCT TCT GAC AAA ACT CAC ACA TCC CCA CCG TCC CCA
    K   S   S*  D   K   T   H   T   S*  P   P   S*  P
    Human IgG₁ Hinge →
509 GCA CCT GAA CTC CTG GGG GGA TCG TCA GTC TTC CTC TTC
    A   P   E   L   L   G   G   S*  S   V   F   L   F
               → Human IgG₁ C_H2 Domain →
548 CCC CCA AAA CCC AAG GAC ACC CTC ATG ATC TCC CGG ACC
    P   P   K   P   K   D   T   L   M   I   S   R   T
```

FIG. 1 (continued)

```
587   CCT GAG GTC ACA TGC GTG GTG GTG GAC GTG AGC CAC GAA
       P   E   V   T   C   V   V   V   D   V   S   H   E

626   GAC CCT GAG GTC AAG TTC AAC TGG TAC GTG GAC GGC GTG
       D   P   E   V   K   F   N   W   Y   V   D   G   V

665   GAG GTG CAT AAT GCC AAG ACA AAG CCG CGG GAG GAG CAG
       E   V   H   N   A   K   T   K   P   R   E   E   Q

704   TAC AAC AGC ACG TAC CGT GTG GTC AGC GTC CTC ACC GTC
       Y   N   S   T   Y   R   V   V   S   V   L   T   V

743   CTG CAC CAG GAC TGG CTG AAT GGC AAG GAG TAC AAG TGC
       L   H   Q   D   W   L   N   G   K   E   Y   K   C

782   AAG GTC TCC AAC AAA GCC CTC CCA GCC CCC ATC GAG AAA
       K   V   S   N   K   A   L   P   A   P   I   E   K

821   ACC ATC TCC AAA GCC AAA GGG CAG CCC CGA GAA CCA CAG
       T   I   S   K   A   K │ G   Q   P   R   E   P   Q
                              └─→ Human IgG₁ C_H3 Domain →

860   GTG TAC ACC CTG CCC CCA TCC CGG GAT GAG CTG ACC AAG
       V   Y   T   L   P   P   S   R   D   E   L   T   K

899   AAC CAG GTC AGC CTG ACC TGC CTG GTC AAA GGC TTC TAT
       N   Q   V   S   L   T   C   L   V   K   G   F   Y

938   CCC AGC GAC ATC GCC GTG GAG TGG GAG AGC AAT GGG CAG
       P   S   D   I   A   V   E   W   E   S   N   G   Q

977   CCG GAG AAC AAC TAC AAG ACC ACG CCT CCC GTG CTG GAC
       P   E   N   N   Y   K   T   T   P   P   V   L   D

1016  TCC GAC GGC TCC TTC TTC CTC TAC AGC AAG CTC ACC GTG
       S   D   G   S   F   F   L   Y   S   K   L   T   V

1055  GAC AAG AGC AGG TGG CAG CAG GGG AAC GTC TTC TCA TGC
       D   K   S   R   W   Q   Q   G   N   V   F   S   C

1094  TCC GTG ATG CAT GAG GCT CTG CAC AAC CAC TAC ACG CAG
       S   V   M   H   E   A   L   H   N   H   Y   T   Q

1133  AAG AGC CTC TCC CTG TCT CCG GGT AAA TGA GTGCGACG
       K   S   L   S   L   S   P   G   K   -

1172  GCCGGCAAGC CCCGCTCCCC GGGCTCTCGC GGTCGCAC GAGGATGCTT
1222  CTAGA
```

METHOD FOR RETARDING PROGRESSION TO DEFINITE RHEUMATOID ARTHRITIS IN SUBJECTS WITH UNDIFFERENTIATED ARTHRITIS

This application is a continuation of U.S. Ser. No. 12/387,359 filed May 1, 2009, which is currently allowed, which claims the benefit of the filing date of U.S. Ser. No. 61/050,336, filed May 5, 2008. The contents of all of the foregoing applications in their entireties are incorporated by reference into the present application.

Throughout this application various publications are referenced. The disclosures of these publications in their entireties are hereby incorporated by reference into this application in order to more fully describe the state of the art to which this invention pertains.

FIELD OF THE INVENTION

The present invention relates generally to the field of immune system diseases, e.g., undifferentiated arthritis (UA). In particular, the invention relates to methods and compositions for treating UA and/or preventing the development of RA in subjects with UA by administering to a subject in need thereof an effective amount of soluble CTLA4 molecule.

BACKGROUND OF THE INVENTION

Rheumatoid arthritis (RA) is the most common inflammatory arthritis, affecting approximately 1% of the population world wide (Wolfe, F., "The epidemiology of drug treatment failure in rheumatoid arthritis", *Baillieres Clin. Rheumatol.*, 9(4):619-632 (November 1995)). Women are 2-3 times more likely to develop disease compared to men, with a peak incidence between the fourth and sixth decades of life (Hochberg, M. C. et al., "Epidemiology of rheumatoid arthritis: update", *Epidemiol. Rev.*, 12:247-252 (1990); Markenson, J. A., "Worldwide trends in the socioeconomic impact and long-term prognosis of rheumatoid arthritis", *Semin. Arthritis Rheum.*, 21(2 Suppl. 1):4-12 (October 1991); Spector, T. D., "Rheumatoid arthritis", *Rheum. Dis. Clin. North Am.*, 16(3):513-537 (August 1990); and Zvaifler, N. J., "Etiology and pathogenesis of rheumatoid arthritis", in *Arthritis and Allied Conditions*, McCarty, D. J., Koopman, W. J., eds. Philadelphia: Lea & Febiger, 723-736 (1993)). While RA is recognized clinically because of the severe inflammation affecting the synovial joints, it is also a systemic disease with frequent extra-articular manifestations. The natural history of RA is unfortunately characterized by joint destruction, impaired physical function and poor health related quality of life.

There is increasing scientific evidence that joint destruction occurs early in RA. Over 90% of subjects have evidence of joint damage by conventional radiography within two years after the diagnosis of RA (Emery, P., "The Optimal Management of Early Rheumatoid Disease: The Key to Preventing Disability", *Br. J. Rheum.*, 33:765-768 (1994)). Joint damage can be detected within weeks of the onset of symptoms using more sensitive techniques such as MRI or ultrasound (McGonagle, D. et al., "The relationship between synovitis and bone changes in early untreated rheumatoid arthritis", *Arthritis Rheum.*, 42:1706-1711 (1999) and Wakefield, R. J. et al., "The value of sonography in the detection of bone erosion in patients with rheumatoid arthritis: A comparative study with conventional radiography", *Arthritis Rheum.*, 43:2761-2770 (2000)). These findings have created an increasing need for therapies which can effectively inhibit the inflammatory processes which cause bone and cartilage loss early on in RA and have placed increasing emphasis on earlier diagnosis and treatment of RA.

However, the 1987 American Rheumatism Association (ARA) criteria for RA are less sensitive and specific when applied to subjects with early inflammatory arthritis compared to subjects with more established disease. Subjects with early inflammatory arthritis may have oligoarthritis rather than polyarthritis, may have symptoms of arthritis for less than six weeks or may initially lack rheumatoid factor, rheumatoid nodules or erosions on conventional radiography (Van Gaalen, F. A. et al., "Autoantibodies to Cyclic Citrullinated Peptides Predict Progression to Rheumatoid Arthritis in Patients with Undifferentiated Arthritis", *Arthritis Rheum.*, 50(3):709-715 (2004)). As a result, these subjects often fail to meet the 1987 diagnostic criteria for RA (or any other rheumatic disease) early on in the disease process. These subjects are then diagnosed with undifferentiated arthritis (UA) by the process of exclusion. Approximately 40% of subjects referred to specialized tertiary care centers designed for the diagnosis and management of early inflammatory arthritis do not meet diagnostic criteria for RA or any other rheumatic disease (Van Gaalen, F. A. et al., "Autoantibodies to Cyclic Citrullinated Peptides Predict Progression to Rheumatoid Arthritis in Patients with Undifferentiated Arthritis", *Arthritis Rheum.*, 50(3):709-715 (2004)). Therefore undifferentiated arthritis is a common clinical entity.

The normal synovium is a tissue that surrounds and separates joint spaces. The lining layer of cells, composed of macrophage-like and fibroblast-like synoviocytes, overlays a thin connective tissue stroma containing sparse numbers of dendritic cells, fibroblasts, mast cells and vascular structures (Konttinen, Y. T. et al., "Characterization of the immunocompetent cells of rheumatoid synovium from tissue sections and eluates", *Arthritis Rheum.*, 24(1):71-79 (January 1981)).

In RA, the synovial tissue becomes markedly thickened and swollen. As the disease progresses, there is gradual proliferation and recruitment of synoviocytes, as well as recruitment of inflammatory cells into the synovium (Konttinen, Y. T. et al., "Characterization of the immunocompetent cells of rheumatoid synovium from tissue sections and eluates", *Arthritis Rheum.*, 24(1):71-79 (January 1981)). Up to 50% of the infiltrating leukocytes in the synovium are T-lymphocytes, primarily CD4+ T cells with an activated/memory phenotype (Konttinen, Y. T. et al., "Characterization of the immunocompetent cells of rheumatoid synovium from tissue sections and eluates", *Arthritis Rheum.*, 24(1):71-79 (January 1981); Forre, O. et al., "Augmented numbers of HLA-DR-positive T lymphocytes in the synovial fluid and synovial tissue of subjects with rheumatoid arthritis and juvenile rheumatoid arthritis: in vivo-activated T lymphocytes are potent stimulators in the mixed lymphocyte reaction", *Scand. J. Immunol.*, 15(2):227-231 (February 1982); Van-Boxel, J. A. et al., "Predominantly T-cell infiltrate in rheumatoid synovial membranes", *N. Engl. J. Med.*, 293(11):517-520 (September 1975); Kidd, B. L. et al., "Immunohistological features of synovitis in ankylosing spondylitis: a comparison with rheumatoid arthritis", *Ann. Rheum. Dis.*, 48(2):92-98 (February 1989); Cush, J. J. et al., "Phenotypic analysis of synovial tissue and peripheral blood lymphocytes isolated from subjects with rheumatoid arthritis", *Arthritis Rheum.*, 31(10):230-238 (October 1988); Laffon, A. et al., "Upregulated expression and function of VLA-4 fibronectin receptors on human activated T cells in rheumatoid arthritis", *J. Clin. Invest.,* 88(2):546-552 (August 1991); and Klareskog, L. et al., "Relationship between HLA DR expressing cells and T lymphocytes of different subsets in rheumatoid synovial tissue", *Scand. J. Immunol.,* 15(5):501-507 (May 1981)). Cells of monocyte/macrophage origin also become prominent in the rheumatoid synovium, accounting for up to 20% of cells, and they too exhibit an activated phenotype (Firestein, G. S. et al., "How important are T cells in chronic rheumatoid synovitis?" *Arthritis Rheum.,* 33(6):768-773 (June 1990) and Firestein, G. S. et al., "Quantitative analysis of cytokine gene expression in rheumatoid", *J. Immunol.,* 144(9):3347-3353 (May 1, 1990)). Monocyte/macrophage-like cells in the rheumatoid synovium produce an array of pro-inflammatory molecules, including the cytokines IL-1, TNF-α, IL-6, GM-CSF as well as proteolytic enzymes including collagenases and matrix metalloproteinases. B-cells, plasma cells and neutrophils account for less than 5% of cells in the rheumatoid synovium, although neutrophils are prominent in the synovial fluid (Konttinen, Y. T. et al., "Characterization of the immunocompetent cells of rheumatoid synovium from tissue sections and eluates", *Arthritis Rheum.,* 24(1):71-79 (January 1981); Forre, O. et al., "Augmented numbers of HLA-DR-positive T lymphocytes in the synovial fluid and synovial tissue of subjects with rheumatoid arthritis and juvenile rheumatoid arthritis: in vivo-activated T lymphocytes are potent stimulators in the mixed lymphocyte reaction", *Scand. J. Immunol.,* 15(2):227-231 (February 1982); and Firestein, G. S. et al., "Quantitative analysis of cytokine gene expression in rheumatoid", *J. Immunol.,* 144(9):3347-3353 (May 1, 1990)).

As synovial proliferation and inflammation advances, the expanding mass of vascular, inflammatory synovial tissue is termed pannus. Pannus is responsible for invading articular cartilage and destroying bone. The products of activated T cells are felt to be the driving factors behind the formation and expansion of pannus (Zvaifler, N. J. et al., "Alternative models of joint destruction in rheumatoid arthritis", *Arthritis Rheum.,* 37(6):783-789 (June 1994)).

The monocyte/macrophage-like cells and dendritic cells in the rheumatoid synovium express both class II MHC as well as costimulatory molecules such as CD80 (B7-1)/CD86 (B7-2), and presumably function as antigen presenting cells (Balsa, A. et al., "Differential expression of the costimulatory molecules B7.1 (CD80) and B7.2 (CD86) in rheumatoid synovial tissue", *Br. J. Rheumatol.,* 35(1):33-37 (January 1996); Liu, M. F. et al., "The presence of costimulatory molecules CD86 and CD28 in rheumatoid arthritis synovium", *Arthritis Rheum.,* 39(1):110-114 (January 1996); Ranheim, E. A. et al., "Elevated expression of CD80 (B7/BB1) and other accessory molecules on synovial fluid mononuclear cell subsets in rheumatoid arthritis", *Arthritis Rheum.,* 37(11):1637-1646 (November 1994); Sfikakis, P. P. et al., "Expression of CD28, CTLA4, CD80, and CD86 molecules in subjects with autoimmune rheumatic diseases: implications for immunotherapy", *Clin. Immunol. Immunopathol.,* 83(3):195-198 (June 1997); and Thomas, R. et al., "Functional differentiation of dendritic cells in rheumatoid arthritis: role of CD86 in the synovium", *J. Immunol.,* 156(8):3074-3086 (Apr. 15, 1996)). Activated CD4+ T cells expressing CD28 are prominent infiltrating cell types in the rheumatoid synovium and commonly are found adjacent to cells that express class II MHC and costimulatory molecules. This suggests an important role for T cell activation/costimulation in the pathogenesis of synovial inflammation. This is consistent with the experimental observation that activated T cells, either through cell to cell contact with synoviocytes and osteoclasts or by the elaboration of secreted cytokines, are important factors in driving synovitis and bone destruction in RA. Taken together, these observations suggest that activated T cells and the costimulatory signals delivered through CD28 play a key role in driving the immunopathology of RA.

The approach to the treatment of RA has evolved towards initiating Disease Modifying Anti-Rheumatic Drug (DMARD) therapy earlier following diagnosis with subsequent optimization of drug therapy in order to have a greater beneficial impact on disease outcome (Redlich, K. et al., "Rheumatoid Arthritis Therapy After Tumor Necrosis Factor and Interleukin-1 Blockade", *Arthritis Rheum.,* 40(12):3308-3319 (2003)). However, no standard of care exists for the treatment of patients with UA (Harrison, B. J. et al., "Natural remission in inflammatory polyarthritis: issues of definition and prediction," *Br. J. Rheumatol.,* 35:1096-1100 (1996)). This is largely due to the inability of the clinician to accurately determine the prognosis of these subjects and their risk for the development of RA based upon commonly used clinical characteristics at presentation. Undifferentiated arthritis may remit spontaneously, progress to a differentiated rheumatic disease such as RA or remain undifferentiated (Quinn, M. A. et al., "Evaluation and management of early inflammatory polyarthritis", *Rheumatology,* Third Edition, MOSBY (Elsevier Limited), 885-891 (2003)). DMARDs are usually not initiated at onset in subjects with UA due to the uncertainty about the prognosis. Instead NSAIDs are traditionally the first drugs to be employed followed by oral corticosteroids. DMARDs are usually used when the symptoms and signs of arthritis are refractory to the first two types of intervention. Hence a "pyramidal" approach has been traditionally employed (Harrison, B. J. et al., "Natural remission in inflammatory polyarthritis: issues of definition and prediction", *Br. J. Rheumatol.,* 35:1096-1100 (1996)). Unfortunately, however, this approach may permit the patient to develop joint damage and destruction before the initiation of potentially disease modifying therapy.

No approved anti-rheumatic therapy has been demonstrated to fundamentally alter the course of undifferentiated arthritis and prevent the development of RA. An agent targeting TNF alpha, infliximab, has been studied in a clinical trial targeting prevention/remission of early RA after a short course of TNF antagonist therapy. However, published data demonstrate that a 6 month course of TNF antagonist therapy does not prevent the progression of UA to RA (Saleem, B. et al., Rheumatology, Academic Unit of Musculoskeletal Disease, Leeds, United Kingdom, *Ann. Rheum. Dis.,* 66(Suppl. II):186 (2007)).

Clearly, there is a need for a treatment that can offer subjects with undifferentiated arthritis at high risk for the development of RA the opportunity to fundamentally alter the course of their disease by selectively targeting T cell activation and preventing the development of RA.

SUMMARY OF THE INVENTION

The present invention provides a method of preventing or inhibiting the development of RA in subjects with UA comprising administering to the subject in need thereof an effective amount of the CTLA4Ig molecule or pharmaceutical composition thereof.

The present invention further provides a method of slowing or retarding the development of RA in subjects with UA comprising administering to the subject in need thereof an effective amount of the CTLA4Ig molecule or pharmaceutical composition thereof.

The present invention also provides a method of treating subjects with UA comprising administering to the subject in need thereof an effective amount of the CTLA4Ig molecule or pharmaceutical composition thereof.

The present invention provides for administration of an effective amount of the CTLA4Ig molecule or pharmaceutical composition thereby relieving the subject having UA of at least one of the symptoms associated with the disease, including reducing: joint swelling, joint tenderness, inflammation, morning stiffness, and pain, and structural damage subsequently decreasing the physical disability.

The methods of the invention also may be used to improve physical function of subjects with UA as assessed by the Health Assessment Questionnaire (HAQ) and/or the health-related quality of life (SF-36) instrument.

The methods of the invention also may be used to inhibit structural damage of the joints in subjects with UA as assessed by erosion and bone marrow edema scoring and/or synovitis scoring of the wrist and hand.

BRIEF DESCRIPTION OF THE DRAWINGS

FIG. 1 presents the nucleotide sequence (SEQ ID NO:1) of a portion of an expression cassette for a CTLA4-Ig molecule. Also shown is the amino acid sequence (SEQ ID NO:2) encoded by the nucleic acid. CTLA4-Ig molecules that can be produced from this expression cassette include molecules having the amino acid sequence of residues: (i) 26-383 of SEQ ID NO:2, (ii) 26-382 of SEQ ID NO:2, (iii) 27-383 of SEQ ID NO:2, or (iv) 26-382 of SEQ ID NO:2, or optionally (v) 25-382 of SEQ ID NO:2, or (vi) 25-383 of SEQ ID NO:2. The expression cassette comprises the following regions: (a) an Oncostatin M signal sequence (nucleotides 11-88 of SEQ ID NO: 1; amino acids 1-26 of SEQ ID NO:2); (b) an extracellular domain of human CTLA4 (nucleotides 89-463 of SEQ ID NO:1; amino acids 27-151 of SEQ ID NO:2); (c) a modified portion of the human IgG1 constant region (nucleotides 464-1159 of SEQ ID NO: 1; amino acids 152-383 of SEQ ID NO:2), including a modified hinge region (nucleotides 464-508 of SEQ ID NO:1; amino acids 152-166 of SEQ ID NO:2), a modified human IgG1 CH2 domain (nucleotides 509-838 of SEQ ID NO:1; amino acids 167-276 of SEQ ID NO:2), and a human IgG1 CH3 domain (nucleotides 839-1159 of SEQ ID NO:1; amino acids 277-383 of SEQ ID NO:2).

DETAILED DESCRIPTION OF THE INVENTION

Figure 2:
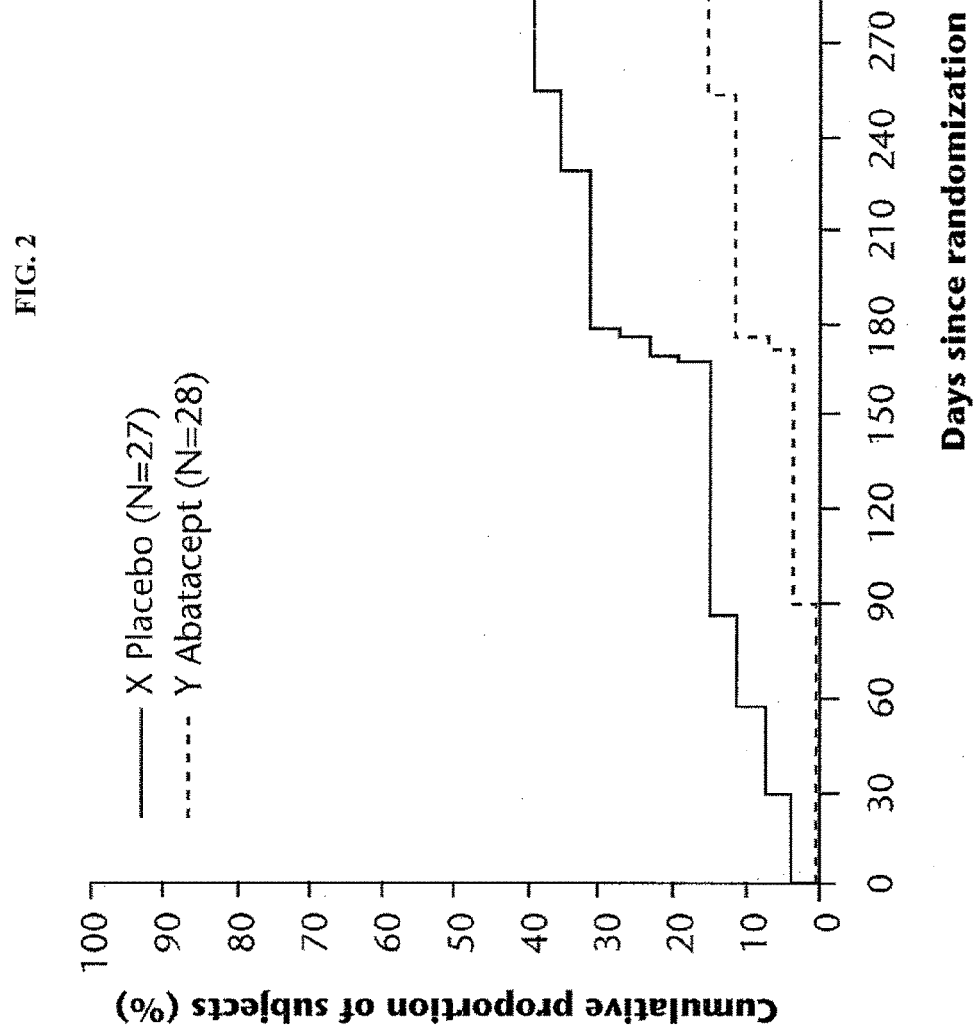
FIG. 2 depicts the time to discontinuation due to development of RA as evaluated in the clinical study described in Example III.

As utilized herein:

The terms "CTLA4-Ig" or "CTLA4-Ig molecule" or "CTLA4Ig molecule" are used interchangeably, and refer to a protein molecule that comprises at least a polypeptide having a CTLA4 extracellular domain or portion thereof and an immunoglobulin constant region or portion thereof. The extracellular domain and the immunoglobulin constant region can be wild-type, or mutant or modified, and mammalian, including human or mouse. The polypeptide can further comprise additional protein domains. A CTLA4-Ig molecule can also refer to multimer forms of the polypeptide, such as dimers, tetramers, and hexamers. A CTLA4-Ig molecule also is capable of binding to CD80 and/or CD86.

The term "B7-1" refers to CD80; the term "B7-2" refers CD86; and the term "B7" refers to both B7-1 and B7-2 (CD80 and CD86). The term "B7-1-Ig" or "B7-1Ig" refers to CD80-Ig; the term "B7-2-Ig" or "B7-2Ig" refers CD86-Ig.

In one embodiment, "CTLA4Ig" refers to a protein molecule having the amino acid sequence of residues: (i) 26-383 of SEQ ID NO:2, (ii) 26-382 of SEQ ID NO:2; (iii) 27-383 of SEQ ID NO:2, or (iv) 27-382 of SEQ ID NO:2, or optionally (v) 25-382 of SEQ ID NO:2, or (vi) 25-383 of SEQ ID NO:2. In monomeric form these proteins can be referred to herein as "SEQ ID NO:2 monomers," or monomers "having a SEQ ID NO:2 sequence". These SEQ ID NO:2 monomers can dimerize, such that dimer combinations can include, for example: (i) and (i); (i) and (ii); (i) and (iii); (i) and (iv); (i) and (v); (i) and (vi); (ii) and (ii); (ii) and (iii); (ii) and (iv); (ii) and (v); (ii) and (vi); (iii) and (iii); (iii) and (iv); (iii) and (v); (iii) and (vi); (iv) and (iv); (iv) and (v); (iv) and (vi); (v) and (v); (v) and (vi); and, (vi) and (vi). These different dimer combinations can also associate with each other to form tetramer CTLA4Ig molecules. These monomers, dimers, tetramers and other multimers can be referred to herein as "SEQ ID NO:2 proteins" or proteins "having a SEQ ID NO:2 sequence". (DNA encoding CTLA4Ig as shown in SEQ ID NO:2 was deposited on May 31, 1991 with the American Type Culture Collection (ATCC®), 10801 University Blvd., Manassas, Va. 20110-2209 under the provisions of the Budapest Treaty, and has been accorded ATCC® accession number ATCC® 68629; a Chinese Hamster Ovary (CHO) cell line expressing CTLA4Ig as shown in SEQ ID NO:2 was deposited on May 31, 1991 with ATCC® identification number CRL-10762).

A "drug substance" refers to the starting material utilized in formulation of the final drug product. Typical CTLA4Ig drug substance composition comprises a protein concentration from 20 mg/ml to 60 mg/ml, pH from 6 to 8 and % HMW species of <5%.

A "formulated bulk solution" refers to the final formulation prior to filling of the container such as the formulated solution prior to filling the vials for lyophilization, or the formulated solution prior to filling the syringe for SC injection.

A "drug product" refers to the final formulation packaged in a container which may be reconstituted before use, such as with a lyophilized drug product; diluted further before use, such as with a liquid drug product; or utilized as is, such as with a SC solution drug product.

"Health Questionnaire Assessments (HAQs)" refers to a set of questions used to evaluate patients for symptoms of disease activity. These symptoms included: joint swelling, joint tenderness, inflammation, morning stiffness, disease activity and disability evaluated by each patient in a self-administered questionnaire regarding their physical well-being and function, disease activity and disability as evaluated a physician, and pain (Fries, J. F. et al., *J. Rheumatology*, 9:789-793 (1982)).

"Medical Outcomes Study Short Form-36 (SF-36)" refers to forms used to evaluate the impact of therapy on health-related quality of life (HRQOL). The SF-36 consists of 36 items which covers four physical and four mental domains (physical function, role-physical, bodily pain, general health, vitality, social function, role emotional, and mental health). These individual domains are used to derive the physical and mental component summary scores which range from 0 to 100, with higher scores indicating better quality of life.

The "1987 Revised American Rheumatism Association (ARA) Criteria for the Classification of Rheumatoid Arthritis (RA)" refers to a set of criteria described in Table 1 below. For classification purposes, a subject is said to have RA if he or she has satisfied at least four of the seven criteria. Criteria 1 through 4 must be present for at least 6 weeks.

TABLE 1

1987 Revised ARA Criteria for the Classification of RA

| Criterion | Definition |
|---|---|
| 1. Morning Stiffness | Morning stiffness in and around the joints lasting at least 1 hour before maximal improvement |
| 2. Arthritis of three or more joint areas | At least three joint areas simultaneously having soft tissue swelling or fluid (not bony overgrowth alone) observed by a physician (the 14 possible joint areas are [right or left] PIP, MCP, wrist elbow, knee, ankle and MTP joints) |
| 3. Arthritis of hand joints | At least one joint area swollen as above in wrist, MCP, or PIP joint |
| 4. Symmetric arthritis | Simultaneous involvement of the same joint areas (as in criterion 2) on both sides of the body (bilateral involvement of PIP, MCP, or MTP joints is acceptable without absolute symmetry) |
| 5. Rheumatoid nodules | Subcutaneous nodules over bony prominences or extensor surfaces, or in juxta-articular regions, observed by a physician |
| 6. Serum rheumatoid factor | Demonstration of abnormal amounts of serum "rheumatoid factor" by any method that has been positive in less than 5 percent of normal control subjects |
| 7. Radiographic changes | Changes typical of RA on PA hand and wrist radiographs, which must include erosions or unequivocal bony decalcification localized to or most marked adjacent to the involved joints (osteoarthritis changes alone do not qualify) |

Abbreviations:
ARA, American Rheumatism Association;
PIP, proximal interphalangeal;
MCP, metacarpophalangeal;
MTP, metatarsophalangeal;
RA, rheumatoid arthritis;
PA, posteroanterior*.

The term "ACR" refers to clinical response studies based on criteria established by the American College of Rheumatology. The ACR Core Data Set and Response Definitions are described in Table 2 below. A subject satisfies the "ACR20" criterion if there was a 20 percent improvement in tender and swollen joint counts and 20 percent improvement in three of five remaining symptoms measured, such as patient and physician global disease changes, pain, physical disability, and an acute phase reactant such as C-reactive Protein (CRP) or Expedited Safety Report (ESR) (Felson, D. T. et al., *Arthritis Rheum.*, 36:729-740 (1993); Felson, D. T. et al., *Arthritis Rheum.*, 38:1-9 (1995)). Similarly, a subject satisfies the "ACR50" or "ACR70" criterion if there was a 50 or 70 percent improvement, respectively, in tender and swollen joint counts and 50 or 70 percent improvement, respectively, in three of five remaining symptoms measured, such as patient and physician global disease changes, pain, physical disability, and an acute phase reactant such as CRP or ESR.

TABLE 2

ACR Core Data Set and Response Definitions

| ACR core data set component | Validated Measurement Tool |
|---|---|
| 1. Tender joint count | Standardized 68 joint count |
| 2. Swollen joint count | Standardized 66 joint count |
| 3. Subject global assessment of pain | A 0-100 mm visual analog scale |
| 4. Subject global assessment of disease activity | A 0-100 mm visual analog scale |
| 5. Physician global assessment of disease activity | A 0-100 mm visual analog scale |
| 6. Subject assessment of physical function | Health Assessment Questionnaire (HAQ) |
| 7. Acute phase reactant value | ESR (Westergren) and C-reactive protein |

A person is diagnosed with undifferentiated arthritis (UA) when they have symptomatic clinical synovitis of two or more joints and possess at least one and not more than three of the criteria for classification of RA of the American Rheumatism Association (1987) described in Table 1.

As used herein, "treat" or "treating" UA means to manage UA by medicinal or other therapies. Treatment of UA may suppress immune-mediated events associated with the disease, ameliorate the symptoms of the disease or disorder, reduce the severity of the disease, alter the course of the disease progression and/or ameliorate or cure the disease. For example, to treat UA may be accomplished by regulating an immune response e.g., by regulating functional CTLA4- and/or CD28-positive cell interactions with B7-positive cells. Alternatively, treating UA may be accomplished by preventing or inhibiting the disease from progressing to RA through the use of the compositions described herein. For example, treating UA includes inhibition of joint erosion as measured by MRI.

Serum samples can be analyzed for CTLA4Ig by an enzyme-linked immunosorbent assay (ELISA).

CTLA4-Ig Monomers and Multimers

CTLA4-Ig molecules can include, for example, CTLA4-Ig proteins in monomer, dimer, trimer, tetramer, pentamer, hexamer, or other multimeric forms. CTLA4-Ig molecules can comprise a protein fusion with at least an extracellular domain of CTLA4 and an immunoglobulin constant region. CTLA4-Ig molecules can have wild-type or mutant sequences, for example, with respect to the CTLA4 extracellular domain and immunoglobulin constant region sequences. CTLA4-Ig monomers, alone, or in dimer, tetramer or other multimer form, can be glycosylated.

In some embodiments, the invention provides populations of CTLA4-Ig molecules that have at least a certain percentage of dimer or other multimer molecules. For example, the invention provides CTLA4-Ig molecule populations that are greater than 90%, 95%, 96%, 97%, 98%, 99%, or 99.5% CTLA4-Ig dimers. In one embodiment, the invention provides a CTLA4-Ig molecule population that comprises from about 95% to about 99.5% CTLA4-Ig dimer and from about 0.5% to about 5% of CTLA4-Ig tetramer. In another embodiment, the CTLA4-Ig molecule population comprises about 98% CTLA4-Ig dimer, about 1.5% CTLA4-Ig tetramer and about 0.5% CTLA4-Ig monomer.

In one embodiment, the invention provides a population of CTLA4-Ig molecules wherein the population is substantially free of CTLA4-Ig monomer molecules. Substantially free of CTLA4-Ig monomer molecules can refer to a population of CTLA4-Ig molecules that have less than 1%, 0.5%, or 0.1% of monomers.

In one embodiment, the invention provides a population of CTLA4-Ig molecules wherein the population is substantially free of CTLA4-Ig multimers that are larger than dimers, such as tetramers, hexamers, etc. Substantially free of CTLA4-Ig multimer molecules larger than dimers can refer to a population of CTLA4-Ig molecules that have less than 6%, 5%, 4%, 3%, 2%, 1%, 0.5%, or 0.1% of CTLA4-Ig multimers larger than dimeric form.

In one embodiment, a CTLA4-Ig monomer molecule can have, for example, the amino acid sequence of: (i) 26-383 of SEQ ID NO:2, (ii) 26-382 of SEQ ID NO:2 (iii) 27-383 of SEQ ID NO:2, or (iv) 27-382 of SEQ ID NO:2, or optionally (v) 25-382 of SEQ ID NO:2, or (vi) 25-383 of SEQ ID NO:2. When an expression cassette comprising the nucleic acid sequence of SEQ ID NO: 1 is expressed in CHO cells, the predominant monomer form expressed has the N-terminus amino acid residue of methionine (residue 27 of SEQ ID NO:2), which corresponds to the N-terminus amino acid residue of wild-type human CTLA4. However, because SEQ ID NO:1 also includes the coding sequence for an Oncostatin M Signal Sequence (nucleotides 11-88 of SEQ ID NO: 1), the expressed protein from SEQ ID NO:1 contains an Oncostatin M Signal Sequence. The signal sequence is cleaved from the expressed protein during the process of protein export from the cytoplasm, or secretion out of the cell. But cleavage can result in N-terminal variants, such as cleavage between amino acid residues 25 and 26 (resulting in an N-terminus of residue 26, i.e., the "Ala variant"), or between amino acid residues 24 and 25 (resulting in an N-terminus of residue 2, i.e., the "Met-Ala variant"), as opposed to cleavage between amino acid residues 26 and 27 (resulting in an N-terminus of residue 27). For example, the Met-Ala variant can be present in a mixture of CTLA4-Ig molecules at about 1%, and the Ala variant can be present in a mixture of CTLA4-Ig molecules at about 8-10%. In addition, the expressed protein from SEQ ID NO:1 can have C-terminus variants due to incomplete processing. The predominant C-terminus is the glycine at residue 382 of SEQ ID NO:2. In a mixture of CTLA4-Ig molecules, monomers having lysine at the C-terminus (residue 383 of SEQ ID NO:2) can be present, for example, at about 4-5%.

A CTLA4-Ig monomer molecule can comprise an extracellular domain of human CTLA4. In one embodiment, the extracellular domain can comprise the nucleotide sequence of nucleotides 89-463 of SEQ ID NO:1 that code for amino acids 27-151 of SEQ ID NO:2. In another embodiment, the extracellular domain can comprise mutant sequences of human CTLA4. In another embodiment, the extracellular domain can comprise nucleotide changes to nucleotides 89-463 of SEQ ID NO:1 such that conservative amino acid changes are made. In another embodiment, the extracellular domain can comprise a nucleotide sequence that is at least 75%, 80%, 85%, 90%, 95%, 96%, 97%, 98%, or 99% identical to nucleotides 89-463 of SEQ ID NO:1.

A CTLA4-Ig monomer molecule can comprise a constant region of a human immunoglobulin. This constant region can be a portion of a constant region; this constant region can have a wild-type or mutant sequence. The constant region can be from human IgG1, IgG2, IgG3, IgG4, IgM, IgA1, IgA2, IgD or IgE. The constant region can be from a light chain or a heavy chain of an immunoglobulin. Where the constant region is from an IgG, IgD, or IgA molecule, the constant region can comprise one or more of the following constant region domains: CL, CH1, hinge, CH2, or CH3. Where the constant region is from IgM or IgE, the constant region can comprise one or more of the following constant region domains: CL, CH1, CH2, CH3, or Ca4. In one embodiment, the constant region can comprise on or more constant region domains from IgG, IgD, IgA, IgM or IgE.

In one embodiment, a CTLA4-Ig monomer molecule comprises a modified human IgG1 hinge region (nucleotides 464-508 of SEQ ID NO: 1; amino acids 152-166 of SEQ ID NO:2) wherein the serines at amino acid residues 156, 162, and 165 of SEQ ID NO:2 have been engineered from cysteines present in the wild-type sequence.

In one embodiment, a CTLA4-Ig monomer molecule comprises a modified human IgG1 CH2 region and a wild-type CH3 region (the modified human IgG1 CH2 domain having nucleotides 509-838 of SEQ ID NO: 1 and amino acids 167-276 of SEQ ID NO:2; the human IgG1 CH3 domain having nucleotides 839-1159 of SEQ ID NO:1 and amino acids 277-383 of SEQ ID NO:2).

In one embodiment, a CTLA4-Ig molecule population comprises monomers having a sequence shown in any one or more of FIG. 7, 8, or 9 of the U.S. Pat. No. 7,094,874, issued on Aug. 22, 2006 and in U.S. Patent Application Publication Nos. 2003/0083246 and 2004/0022787, which are hereby incorporated by reference in its entirety.

In one embodiment, a CTLA4-Ig tetramer molecule comprises two pairs or two dimers of CTLA4-Ig polypeptides, wherein each polypeptide has one of the following amino acid sequences: (i) 26-383 of SEQ ID NO:2, (ii) 26-382 of SEQ ID NO:2, (iii) 27-383 of SEQ ID NO:2, or (iv) 27-382 of SEQ ID NO:2, or optionally (v) 25-382 of SEQ ID NO:2, or (vi) 25-383 of SEQ ID NO:2. Each member of the pair of polypeptides or dimer is covalently linked to the other member, and the two pairs of polypeptides are non-covalently associated with one another thereby forming a tetramer. Such tetramer molecules are capable of binding to CD80 or CD86.

In another embodiment, such tetramer molecules can bind to CD80 or CD86 with an avidity that is at least 2-fold greater than the binding avidity of a CTLA4-Ig dimer (whose monomers have one of the above amino acid sequences) to CD80 or CD86. In another embodiment, such tetramer molecules can bind to CD80 or CD86 with an avidity that is at least 2-fold greater than the binding affinity or avidity of wild-type CTLA4 to CD80 or CD86. Such greater avidity can contribute to higher efficacy in treating immune disorders and other diseases as described below. In addition, greater or improved avidity can produce the result of higher potency of a drug. For example, a therapeutic composition comprising CTLA4-Ig tetramer would have a higher avidity and therefore higher potency than the same amount of a therapeutic composition having CTLA4-Ig monomer. In another embodiment, such tetramer molecules can have at least a 2-fold greater inhibition on T cell proliferation as compared to a CTLA4-Ig dimer (whose monomers have one of the above amino acid sequences). In another embodiment, such tetramer molecules can have at least a 2-fold greater inhibition on T cell proliferation as compared to a wild-type CTLA4 molecule.

T cell proliferation can be measured using standard assays known in the art. For example, one of the most common ways to assess T cell proliferation is to stimulate T cells via antigen or agonistic antibodies to TCR and to measure, for example, the incorporation of titrated thymidine (3H-TdR) in proliferating T cells or the amount of cytokines released by proliferating T cells into culture. The inhibitory effect of CTLA4-Ig molecules upon T cell activation or proliferation can thereby be measured.

The affinity of a CTLA4-Ig molecule is the strength of binding of the molecule to a single ligand, including CD80, CD86, or CD8OIg or CD86Ig fusion proteins. The affinity of CTLA4-Ig to ligands can be measured by using, for example, binding interaction analysis (BIA) based on surface plasmon technique. Aside from measuring binding strength, it permits real time determination of binding kinetics, such as association and dissociation rate constants. A sensor chip, consisting of a glass slide coated with a thin metal film, to which a surface matrix is covalently attached, is coated with one of the interactants, i.e., CTLA4-Ig or one of the ligands. A solution containing the other interactant is allowed to flow over its surface. A continuous light beam is directed against the other side of the surface, and its reflection angle is measured. On binding of CTLA4-Ig to the ligand, the resonance angle of the light beam changes (as it depends on the refractive index of the medium close to the reactive side of the sensor, which in turn is directly correlated to the concentration of dissolved material in the medium). It is subsequently analyzed with the aid of a computer.

In one embodiment, CTLA4-Ig binding experiments can be performed by surface plasmon resonance (SPR) on a BIAcore instrument (BIAcore AG, Uppsala, Sweden). CTLA4-Ig can be covalently coupled by primary amine groups to a carboxymethylated dextran matrix on a BIAcore sensor chip, thereby immobilizing CTLA4-Ig to the sensor chip. Alternatively, an anti-constant region antibody can be used to immobilize CTLA4-Ig indirectly to the sensor surface via the Ig fragment. Thereafter, ligands are added to the chip to measure CTLA4-Ig binding to the ligands. Affinity measurements can be performed, for example, as described in van der Merwe, P. et al., *J. Exp. Med.*, 185(3):393-404 (1997).

The avidity of CTLA4-Ig molecules can also be measured. Avidity can be defined as the sum total of the strength of binding of two molecules or cells to one another at multiple sites. Avidity is distinct from affinity which is the strength of binding one site on a molecule to its ligand. Without being bound by theory, higher avidity of CTLA4-Ig molecules can lead to increased potency of inhibition by CTLA4-Ig molecules on T-cell proliferation and activation. Avidity can be measured, for example, by two categories of solid phase assays: a) competitive inhibition assays, and b) elution assays. In both of them the ligand is attached to a solid support. In the competitive inhibition assay, CTLA4-Ig molecules are then added in solution at a fixed concentration, together with free ligand in different concentrations, and the amount of ligand which inhibits solid phase binding by 50% is determined. The less ligand needed, the stronger the avidity. In elution assays, the ligand is added in solution. After obtaining a state of equilibrium, a chaotrope or denaturant agent (e.g., isothiocyanate, urea, or diethylamine) is added in different concentrations to disrupt CTLA4-Ig/ligand interactions. The amount of CTLA4-Ig resisting elution is determined thereafter with an ELISA. The higher the avidity, the more chaotropic agent is needed to elute a certain amount of CTLA4-Ig. The relative avidity of a heterogeneous mixture of CTLA4-Ig molecules can be expressed as the avidity index (AI), equal to the concentration of eluting agent needed to elute 50% of the bound CTLA4-Ig molecules. Refined analysis of data can be performed by determining percentages of eluted CTLA4-Ig at different concentrations of the eluting agent.

Methods for Producing the CTLA4Ig Molecules of the Invention

Expression of CTLA4Ig molecules can be in prokaryotic cells. Prokaryotes most frequently are represented by various strains of bacteria. The bacteria may be a gram positive or a gram negative. Typically, gram-negative bacteria such as *E. coli* are preferred. Other microbial strains may also be used.

Sequences, described above, encoding CTLA4Ig molecules can be inserted into a vector designed for expressing foreign sequences in prokaryotic cells such as *E. coli*. These vectors can include commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang et al., *Nature*, 198:1056 (1977)), the tryptophan (tip) promoter system (Goeddel et al., *Nucleic Acids Res.*, 8:4057 (1980)) and the lambda derived $P_L$ promoter and N-gene ribosome binding site (Shimatake et al., *Nature*, 292:128 (1981)).

Such expression vectors will also include origins of replication and selectable markers, such as a beta-lactamase or neomycin phosphotransferase gene conferring resistance to antibiotics, so that the vectors can replicate in bacteria and cells carrying the plasmids can be selected for when grown in the presence of antibiotics, such as ampicillin or kanamycin.

The expression plasmid can be introduced into prokaryotic cells via a variety of standard methods, including but not limited to $CaCl_2$-shock (Cohen, *Proc. Natl. Acad. Sci. USA*, 69:2110 (1972), and Sambrook et al., eds., *Molecular Cloning: A Laboratory Manual*, 2nd Edition, Cold Spring Harbor Press (1989)) and electroporation.

In accordance with the practice of the invention, eukaryotic cells are also suitable host cells. Examples of eukaryotic cells include any animal cell, whether primary or immortalized, yeast (e.g., *Saccharomyces cerevisiae, Schizosaccharomyces pombe,* and *Pichia pastoris*), and plant cells. Myeloma, COS and CHO cells are examples of animal cells that may be used as hosts. Particular CHO cells include, but are not limited to, DG44 (Chasin et al., *Som. Cell. Molec. Genet.*, 12:555-556 (1986); Kolkekar, *Biochemistry*, 36:10901-10909 (1997)), CHO-K1 (ATCC® No. CCL-61), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), and RR-CHOK1 designated ECACC 92052129 (CAMR, Salisbury, Wiltshire, UK). Illustrative plant cells include tobacco (whole plants, cell culture, or callus), corn, soybean, and rice cells. Corn, soybean, and rice seeds are also acceptable.

Nucleic acid sequences encoding CTLA4Ig molecules described above can also be inserted into a vector designed for expressing foreign sequences in a eukaryotic host. The regulatory elements of the vector can vary according to the particular eukaryotic host.

Commonly used eukaryotic control sequences for use in expression vectors include promoters and control sequences compatible with mammalian cells such as, for example, CMV promoter (CDM8 vector) and avian sarcoma virus (ASV) (πLN vector). Other commonly used promoters include the early and late promoters from Simian Virus 40 (SV40) (Fiers et al., *Nature*, 273:113 (1973)), or other viral promoters such as those derived from polyoma, Adenovirus 2, and bovine papilloma virus. An inducible promoter, such as hMTII (Karin et al., *Nature*, 299:797-802 (1982)) may also be used.

Vectors for expressing CTLA4Ig molecules in eukaryotes may also carry sequences called enhancer regions. These are important in optimizing gene expression and are found either upstream or downstream of the promoter region.

Examples of expression vectors for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene)), retroviral vectors (e.g., pFB vectors (Stratagene)), pcDNA-3 (Invitrogen) or modified forms thereof, adenoviral vectors; Adeno-associated virus vectors, baculovirus vectors, yeast vectors (e.g., pESC vectors (Stratagene)).

Nucleic acid sequences encoding CTLA4Ig molecules can integrate into the genome of the eukaryotic host cell and replicate as the host genome replicates. Alternatively, the vector carrying CTLA4Ig molecules can contain origins of replication allowing for extrachromosomal replication.

For expressing the nucleic acid sequences in *Saccharomyces cerevisiae*, the origin of replication from the endogenous yeast plasmid, the 2μ circle can be used. (Broach, *Meth. Enzymol.*, 101:307 (1983)). Alternatively, sequences from the yeast genome capable of promoting autonomous replication can be used (see, for example, Stinchcomb et al., *Nature*, 282:39 (1979)); Tschemper et al., *Gene*, 10:157 (1980); and Clarke et al., *Meth. Enzymol.*, 101:300 (1983)).

Transcriptional control sequences for yeast vectors include promoters for the synthesis of glycolytic enzymes (Hess et al., *J. Adv. Enzyme Reg.*, 7:149 (1968) and Holland et al., *Biochemistry*, 17:4900 (1978)). Additional promoters known in the art include the CMV promoter provided in the CDM8 vector (Toyama et al., *FEBS*, 268:217-221 (1990)); the promoter for 3-phosphoglycerate kinase (Hitzeman et al., *J. Biol. Chem.*, 255:2073 (1980)), and those for other glycolytic enzymes.

Other promoters are inducible because they can be regulated by environmental stimuli or the growth medium of the cells. These inducible promoters include those from the genes for heat shock proteins, alcohol dehydrogenase 2, isocytochrome C, acid phosphatase, enzymes associated with nitrogen catabolism, and enzymes responsible for maltose and galactose utilization.

Regulatory sequences may also be placed at the 3' end of the coding sequences. These sequences may act to stabilize messenger RNA. Such terminators are found in the 3' untranslated region following the coding sequences in several yeast-derived and mammalian genes.

Illustrative vectors for plants and plant cells include, but are not limited to, *Agrobacterium* $T_i$ plasmids, cauliflower mosaic virus (CaMV), and tomato golden mosaic virus (TGMV).

Mammalian cells can be transformed by methods including but not limited to, transfection in the presence of calcium phosphate, microinjection, electroporation, or via transduction with viral vectors.

Methods for introducing foreign DNA sequences into plant and yeast genomes include (1) mechanical methods, such as microinjection of DNA into single cells or protoplasts, vortexing cells with glass beads in the presence of DNA, or shooting DNA-coated tungsten or gold spheres into cells or protoplasts; (2) introducing DNA by making cell membranes permeable to macromolecules through polyethylene glycol treatment or subjection to high voltage electrical pulses (electroporation); or (3) the use of liposomes (containing cDNA) which fuse to cell membranes.

U.S. Patent Application Publication No. 2005/0019859 and U.S. Pat. No. 7,332,303 teach processes for the production of proteins of the invention, specifically recombinant glycoprotein products, by animal or mammalian cell cultures and are herein incorporated by reference.

Following the protein production phase of the cell culture process, CTLA4Ig molecules are recovered from the cell culture medium using techniques understood by one skilled in the art. In particular, the CTLA4Ig molecule is recovered from the culture medium as a secreted polypeptide.

The culture medium is initially centrifuged to remove cellular debris and particulates. The desired protein subsequently is purified from contaminant DNA, soluble proteins, and polypeptides, with the following non-limiting purification procedures well-established in the art: SDS-PAGE; ammonium sulfate precipitation; ethanol precipitation; fractionation on immunoaffinity or ion-exchange columns; reverse phase HPLC; chromatography on silica or on an anion-exchange resin such as QAE or DEAE; chromatofocusing; gel filtration using, for example, SEPHADEX® G-75 column; and protein A SEPHAROSE® columns to remove contaminants such as IgG. Addition of a protease inhibitor, such as phenyl methyl sulfonyl fluoride (PMSF), or a protease inhibitor cocktail mix also can be useful to inhibit proteolytic degradation during purification. A person skilled in the art will recognize that purification methods suitable for a protein of interest, for example a glycoprotein, can require alterations to account for changes in the character of the protein upon expression in recombinant cell culture.

Purification techniques and methods that select for the carbohydrate groups of the glycoprotein are also of utility within the context of the present invention. For example, such techniques include, HPLC or ion-exchange chromatography using cation- or anion-exchange resins, wherein the more basic or more acidic fraction is collected, depending on which carbohydrate is being selected for. Use of such techniques also can result in the concomitant removal of contaminants.

The purification method can further comprise additional steps that inactivate and/or remove viruses and/or retroviruses that might potentially be present in the cell culture medium of mammalian cell lines. A significant number of viral clearance steps are available, including but not limited to, treating with chaotropes such as urea or guanidine, detergents, additional ultrafiltration/diafiltration steps, conventional separation, such as ion-exchange or size exclusion chromatography, pH extremes, heat, proteases, organic solvents or any combination thereof.

The purified CTLA4Ig molecule require concentration and a buffer exchange prior to storage or further processing. A Pall Filtron TFF system may be used to concentrate and exchange the elution buffer from the previous purification column with the final buffer desired for the drug substance.

In one aspect, purified CTLA4Ig molecules, which have been concentrated and subjected to diafiltration step, can be filled into 2-L BIOTAINER® bottles, 50-L bioprocess bag or any other suitable vessel. CTLA4Ig molecules in such vessels can be stored for about 60 days at 2° to 8° C. prior to freezing. Extended storage of purified CTLA4Ig molecules at 2° to 8° C. may lead to an increase in the proportion of HMW species. Therefore, for long-term storage, CTLA4Ig molecules can be frozen at about −70° C. prior to storage and stored at a temperate of about −40° C. The freezing temperature can vary from about −50° C. to about −90° C. The freezing time can vary and largely depends on the volume of the vessel that contains CTLA4Ig molecules, and the number of vessels that are loaded in the freezer. For example, in one embodiment, CTLA4Ig molecules are in 2-L BIOTAINER® bottles. Loading of less than four 2-L BIOTAINER® bottles in the freezer may require from about 14 to at least 18 hours of freezing time. Loading of at least four bottles may require from about 18 to at least 24 hours of freezing time. Vessels with frozen CTLA4Ig molecules are stored at a temperature from about −35° C. to about −55° C. The storage time at a temperature of about −35° C. to about −55° C. can vary and can be as short as 18 hours. The frozen drug substance can be thawed in a control manner for formulation of drug product.

Co-pending U.S. Patent Application Ser. No. 60/752,267, filed on Dec. 20, 2005 and PCT/US2006/049074 filed on Dec. 19, 2006 teach processes for the production of proteins of the invention, specifically recombinant glycoprotein products, by animal or mammalian cell cultures and is herein incorporated by reference.

Pharmaceutical Composition

The methods of the present invention utilizes pharmaceutical compositions comprising the CTLA4Ig molecules admixed with an acceptable carrier or adjuvant which is known to those of skill of the art. The pharmaceutical compositions preferably include suitable carriers and adjuvants which include any material which when combined with the CTLA4Ig molecule retains the molecule's activity and is non-reactive with the subject's immune system. These carriers and adjuvants include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, phosphate buffered saline solution, water, emulsions (e.g., oil/water emulsion), salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Other carriers may also include sterile solutions; tablets, including coated tablets and capsules. Typically such carriers contain excipients such as starch, milk, sugar (e.g., sucrose, glucose, maltose), certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Such compositions may also be formulated within various lipid compositions, such as, for example, liposomes as well as in various polymeric compositions, such as polymer microspheres.

Formulations comprising soluble CTLA4 molecules are described in copending U.S. Provisional Patent Application Ser. No. 60/752,150 filed Dec. 20, 2005 and PCT/US2006/062297 filed Dec. 19, 2006 are hereby incorporated by reference into this application. As described in copending U.S. Provisional Patent Application Ser. No. 60/752,150, soluble CTLA4 molecules may be formulated for IV and subcutaneous applications. Briefly, a suitable subcutaneous (SC) formulation comprises CTLA4Ig molecules at a protein concentration of at least 100 mg/ml in combination with a sugar at stabilizing levels in an aqueous carrier.

An example of a CTLA4Ig SC drug product that is delivered via a pre-filed syringe is provided in Table 3 below.

TABLE 3

Composition of CTLA4Ig SC Drug Product, 125 mg/ml (125 mg/syringe)

| Component | Amount (mg/syringe) |
|---|---|
| CTLA4Ig | 125 |
| Sucrose | 170 |
| Poloxamer 188 | 8.0 |
| Sodium phosphate monobasic, monohydrate | 0.143 |
| Sodium phosphate dibasic, anhydrous | 0.971 |
| Water for Injection | q.s. to 1. ml |

Examples I and II of the instant specification describe the manufacture of an intravenous (IV) and subcutaneous formulation of CTLA4Ig useful in the methods of the invention. An example of the CTLA4Ig lyophilized formulation utilized in the method of the invention described in Example III is listed below.

TABLE 4

Composition of Lyophilized CTLA4Ig (250 mg/vial) Drug Product

| Component | Amount (mg/vial)$^a$ |
|---|---|
| CTLA4Ig | 262.5 |
| Maltose monohydrate | 525 |
| Sodium phosphate monobasic, monohydrate$^b$ | 18.1 |
| Sodium chloride$^b$ | 15.3 |
| Hydrochloric Acid | Adjust to 7.5 |
| Sodium hydroxide | Adjust to 7.5 |

$^a$Includes a 5% overfill for vial, needle, syringe loss.
$^b$These components are present in the CTLA4Ig drug substance solution.

The lyophilized drug product may be constituted with an aqueous carrier. The aqueous carrier of interest herein is one which is pharmaceutically acceptable (safe and non-toxic for administration to a human) and is useful for the preparation of a liquid formulation, after lyophilization. Typically, the lyophilized drug product is constituted to about 25 mg/ml with 10 ml of either Sterile Water for Injection, USP (SWFI) or 0.9% Sodium Chloride Injection, USP. The constituted solution is further diluted to drug product concentrations between 1 and 10 mg/ml with 0.9% Sodium Chloride Injection, USP. The diluted drug product for injection is isotonic and suitable for administration by intravenous infusion.

Article of Manufacture

In another embodiment of the invention, an article of manufacture is provided which contains the drug product and preferably provides instructions for its use. The article of manufacture comprises a container. Suitable containers include, for example, bottles, vials, syringes and test tubes. The container may be formed from a variety of materials such as glass, plastic or metals.

The container holds the lyophilized or liquid formulations. The label on, or associated with, the container may indicate directions for reconstitution and/or use. For example, the label may indicate that the 250 mg/vial drug product is to be reconstituted to protein concentrations as described above. The label may further indicate that the SC formulation is useful or intended for subcutaneous administration. The container holding the formulation may be a multi-use vial, which allows for repeat administrations (e.g., from 2-6 administrations) of, for example, the subcutaneous formulation. Alternatively, the container may be a pre-filled syringe containing, for example, the subcutaneous formulation.

The article of manufacture may further comprise a second container comprising, for example, a suitable carrier for the lyophilized formulation.

The article of manufacture may further include other materials desirable from a commercial and user standpoint, including other buffers, diluents, filters, needles, syringes, and package inserts with instructions for use.

Silicone free syringes are preferably utilized for surfactant free drug product, such as upon reconstitution of lyophilized drug product and/or transfer of the solutions from the vial to the intravenous bag and may be co-packaged with the drug product vial.

Methods of Use

The present invention provides a method of preventing or inhibiting the development of RA in subjects with UA comprising administering to the subject in need thereof an effective amount of the CTLA4Ig molecule or pharmaceutical composition thereof.

The present invention further provides a method of slowing or retarding the development of RA in subjects with UA comprising administering to the subject in need thereof an effective amount of the CTLA4Ig molecule or pharmaceutical composition thereof.

The present invention also provides a method of treating subjects with UA comprising administering to the subject in need thereof an effective amount of the CTLA4Ig molecule or pharmaceutical composition thereof.

Administration of an effective amount of the CTLA4Ig molecule or pharmaceutical composition thereby relieving the subject of at least one of the symptoms associated with the disease, including reducing: joint swelling, joint tenderness, inflammation, morning stiffness, and pain, and structural damage subsequently decreasing the physical disability.

The methods of the invention also may be used to improve physical function of subjects with UA as assessed by the Health Assessment Questionnaire (HAQ) and/or the health-related quality of life (SF-36) instrument.

The methods of the invention also may be used to inhibit structural damage of the joints in subjects with UA as assessed by erosion and bone marrow edema scoring and/or synovitis scoring of the wrist and hand.

The amount of symptom relief provided by the present invention can be measured using any of the accepted criteria established to measure and document symptom relief in a clinical setting. Acceptable criteria for measuring symptom relief may include scores based on the criteria established by the American College of Rheumatology (e.g., ACR 20), the four measures of symptom relief (in: "CDER Guideline for the Clinical Evaluation of Anti-Inflammatory and Antirheumatic Drugs—FDA 1988"), and the Health Assessment Questionnaire (HAQ) (Fries, J. F. et al., *J. Rheumatology*, 9:789-793 (1982)). For a general description of these criteria, see *Guidance for Industry: Clinical Development Programs for Drugs, Devices, and Biological products for the Treatment of Rheumatoid Arthritis (RA)* (February 1999).

The present invention provides various methods, local or systemic, for administering the CTLA4Ig molecule alone or in conjunction with other therapeutic drugs. The methods include intravenous, intramuscular, intraperitoneal, oral, inhalation and subcutaneous methods, as well as implantable pump, continuous infusion, gene therapy, liposomes, suppositories, topical contact, vesicles, capsules and injection methods. The CTLA4Ig, compounded with a carrier, is commonly lyophilized for storage and is reconstituted with water or a buffered solution prior to administration. As is standard practice in the art, the compositions of the invention may be administered to the subject in any pharmaceutically acceptable form.

The most effective mode of administration and dosage regimen for the formulations of this invention depends upon the patient's health and response to treatment and the judgment of the treating physician. In accordance with the practice of the invention an effective amount for treating a subject is an amount about 0.1 to 100 mg/kg weight of a subject. In another embodiment, the effective amount is an amount about 0.1 to 20 mg/kg weight of a subject, preferably 1 to 10 mg/kg weight of a subject. In a specific embodiment, the effective amount of CTLA4Ig is about 2 mg/kg weight of a subject. In another specific embodiment, the effective amount of CTLA4Ig is about 10 mg/kg weight of a subject. In another specific embodiment, an effective amount of CTLA4Ig is 500 mg for a subject weighing less than 60 kg, 750 mg for a subject weighing between 60-100 kg and 1000 mg for a subject weighing more than 100 kg.

The CTLA4Ig molecule formulations of the invention may be administered to a subject in an amount and for a time (e.g., length of time and/or multiple times) sufficient to block endogenous B7 (e.g., CD80 and/or CD86) molecules from binding their respective ligands, in the subject. Blockage of endogenous B7/ligand binding thereby inhibits interactions between B7-positive cells (e.g., CD80- and/or CD86-positive cells) with CD28- and/or CTLA4-positive cells. Accordingly, dosages of the agents can vary depending on the subject and the mode of administration, U.S. Patent Application Publication Nos. 2003/0083246 and 2004/0022787 teach dosage and administration schedules for CTLA4Ig having the amino acid sequence shown in SEQ ID NO:2 for treating rheumatic diseases, such as rheumatoid arthritis. All are herein incorporated by reference.

An effective amount of CTLA4Ig molecule may be administered to a subject daily, weekly, monthly and/or yearly, in single or multiple times per hour/day/week/month/year, depending on need. For example, in one embodiment, an effective amount of the CTLA4Ig molecule may initially be administered once every two weeks for a month, and then once every month thereafter or Days 1, 15, 29 and monthly thereafter. A +/−3 day window is allowed for earlier doses (i.e., Days 15 and 29). A +/−7 day window is allowed for the monthly doses thereafter.

Alternatively, one knowledgeable in the art would be able to modify the administration regimen in response to the patients risk status and/or response to the therapy. For example, the regimen described above could be modified by adding administration day 5 to the regimen.

As used herein, "four weeks," "month", "months" or "monthly" refers to a period of 28±7 days.

Typically, doses of the CTLA4Ig molecule formulation of the invention are based on body weight, and administration regimens may be dictated by the target serum trough profiles. Typically, target trough serum concentration of CTLA4Ig molecules of the invention between about 3 µg/mL and about 35 µg/mL will be sufficient to treat UA or prevent the development of RA in subjects with UA, preferably between about 5 µg/mL and about 30 µg/mL, more preferably between about 10 µg/mL and about 30 µg/mL. One knowledgeable in the art would be able to adjust the dosage and/or administration schedule of CTLA4Ig to achieve the desired serum trough concentrations.

The administration of the molecules or pharmaceutical compositions of the invention can be via a 30 minute to one or more hour intravenous infusion. Alternatively, single to multiple subcutaneous injections can deliver the required dosage.

The CTLA4Ig molecules of the invention may be administered concomitantly or sequentially in conjunction with other immunosuppressive/immunomodulatory therapy, e.g., as herein specified, dosages of the co-administered immunosuppressant, or immunomodulatory compound will of course vary depending on the type of co-drug employed.

Non-steroidal anti-inflammatory drugs (NSAIDs) may be administered in concomitantly or sequentially in conjunction with the CTLA4Ig molecule of the invention. NSAIDs reduce inflammatory reactions in a subject. NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, meloxicam and tramadol.

Corticosteroids may be administered concomitantly or sequentially in conjunction with the CTLA4Ig molecule of the invention. For example, stable low dose oral corticosteroid (equivalent to $\leq 0$ mg prednisone daily), or high dose corticosteroids administered every six months as an oral course (equivalent to 20 mg/day prednisone daily for a maximum of two weeks), or a single IM (intramuscular) dose or a single IA (intra-articular) dose.

Examples of corticosteroids include but are not limited to, betamethasone, budesonide, cortisol, cortisone, dexamethasone, hydrocritisone, methylprednisolone, prednisolone, prednisone and triamcinolone.

Typically, the standard dosages and administration regimen of the co-administered drags described above are not influenced by the addition of the CTLA4Ig molecules of the invention to the treatment regimen. However, one knowledgeable in the art may prescribe lower doses of the co-administered drugs due to the incorporation of the less toxic CTLA4Ig molecules of the invention into the treatment regimen. Prescribing information may be based on the package insert for each co-administered drag.

As discussed previously, joint destruction occurs early in RA. This insight has highlighted the need for therapies which can fundamentally alter and not merely suppress the inflammatory processes which cause debilitating symptoms and structural damage early on in the course of RA. Consequently, this has placed increasing emphasis on earlier diagnosis and treatment of RA. However, the 1987 ARA criteria for RA are less sensitive and specific when applied to subjects with early inflammatory arthritis and these subjects are then diagnosed with undifferentiated arthritis, a common clinical problem.

It has been recently demonstrated that subjects with UA who are also positive for antibodies against cyclic citrullinated peptides (anti-CCP2 positive) are at high risk for the development of RA as soon as one year after observation (Van Gaalen, F. A. et al., "Autoantibodies to Cyclic Citrullinated Peptides Predict Progression to Rheumatoid Arthritis in Patients with Undifferentiated Arthritis", *Arthritis Rheum.*, 50(3):709-715 (2004)). A positive test for the presence of serum antibodies against cyclic citrullinated peptides has a higher predictive value for the development of RA than more traditional criteria, such as the presence or absence of rheumatoid factor. 83% of UA subjects who were positive for anti-CCP antibodies developed RA at one year, compared with 18% of anti-CCP negative controls. This finding suggests that a sub-population of subjects with UA can be readily identified who will be at high risk for development of RA and who therefore would be ideal candidates for targeted therapy aimed at the underlying mechanisms driving inflammation and joint destruction in RA. Such an approach could prevent the development of joint damage, functional disability and subsequent impaired quality of life that unfortunately characterizes the natural history of RA.

Example III and IV describe a clinical study designed to compare the efficacy of CTLA4Ig with placebo in preventing the development of RA in subjects with recent onset undifferentiated arthritis who are at high risk for the development of RA.

The clinical is a randomized, double-blind, placebo-controlled, two-arm parallel design study of 12 months duration to the primary endpoint and 24 months to secondary endpoint. Subjects are randomized 1:1 to receive either CTLA4Ig or placebo for the first six months of the study. Randomization is stratified into two groups based on the presence or absence of erosions.

The subjects in this study were carefully screened to ensure that they had recent-onset UA (i.e., presence of arthritis symptoms for <18 months), were positive for anti-CCP2 antibodies, did not meet diagnostic criteria for any other rheumatic disease, and had not received more treatment with DMARDs for longer than 2 weeks or any biologic drug indicated for RA. The study was designed to investigate whether a relatively short, 6-month treatment period with CTLA4Ig monotherapy prevented the progression to RA within 1 year or 2 years after the start of treatment. In addition, the effects of CTLA4Ig on disease activity, physical function, health-related quality of life, and PD biomarker activity in subjects with UA was explored and compared to placebo both during the 6-month treatment period and for up to 18 months after the last dose of study medication. The inclusion of an 18-month untreated observation period after the last dose of study medication permitted evaluation of the persistence of any observed effects of CTLA4Ig treatment. The use of NSAIDs and stable low dose oral corticosteroids (–<10 mg/day prednisone or equivalent), as well as limited use of high dose corticosteroid therapy, were permitted during both the treatment and observation periods. Subjects who developed RA at any time were discontinued from the study and could receive standard of care.

Because of strict enrollment criteria, which limited randomization to 57 subjects (56 of whom were treated), formal statistical hypothesis testing was not done. Results of this study, however, were generally consistent across multiple outcome measures of efficacy (clinical, radiological, MRI, and biomarker activity) in favor of CTLA4Ig over placebo, and provide evidence that CTLA4Ig, given IV monthly at a dose of 10 mg/kg based on body weight for 6 months, slows the progression from UA to RA. The therapeutic benefit of CTLA4Ig appeared to persist for as up to 18 months after drug discontinuation.

The proportion of subjects who developed RA by Month 12 was lower for the group who received CTLA4Ig (12/27, 46.2%) than for the placebo group (t6/24, 66.7%) (20.5% treatment difference; 95% CI: −47.4%, +7.8%). By Month 24, 87.5% (12/24) of subjects with UA had developed RA in the placebo group compared with 73.9% (17/23) of subjects who had received a 6-month course of CTLA4Ig treatment (13.6% treatment difference; 95% CI: −37.6%, +10.8%). The weight-tiered 10 mg/kg dose of CTLA4Ig used in this study of subjects with UA is analogous to the 10 mg/kg dosage approved for the treatment of RA in adults.

In this population of subjects with UA, treatment with CTLA4Ig improved physical function and physician-reported disease activity. At Month 6, more than twice as many subjects treated with CTLA4Ig compared with placebo had achieved a clinically meaningful improvement in physical function (HAQ-DI) (62% vs 24%) or had disease remission as indicated by a DAS-28 (CRP) score of <2.6 (71% vs 35%). The numerically larger improvements in ILAQ-DI and DAS 28 (CRP) seen at the end of the study treatment period with CTLA4Ig were still evident after 6 and 18 months of untreated follow-up, although treatment group differences with placebo were smaller at Months 12 and 24. Radiographic evaluations using gandolinium-enhanced MR images of the hand and wrist and conventional radiographs of the hands and feet, indicated minimal disease progression during the study drug treatment period among subjects receiving CTLA4Ig.

Notably, following 6 months of treatment with CTLA4Ig, serum levels of anti-CCP2 antibodies were reduced, and this reduction was still evident after 6 months with no study drug treatment. By comparison, anti-CCP2 antibodies levels were increased in the placebo group. Anti-CCP2 antibodies are highly predictive of the future development of RA in both healthy subjects and patients with undifferentiated arthritis.

A conservative approach to treatment of early UA has been advocated, limiting the use of DMARDs and subsequently, biologies to only those patients whose arthritis symptoms and signs are refractory to NSAIDs and low-dose corticosteroids. In this study of 56 subjects with UA, CTLA4Ig was well tolerated by individuals with very early stage disease. During the 6-month study treatment period, AEs were reported at similar rates for the CTLA4Ig and placebo groups, no AE resulted in death, and equally, low numbers of subjects in both treatment groups had a SAE (1 in each treatment group) or were discontinued due to an AE (1 in each treatment group). Furthermore, there was no evidence for a greater risk of infections with CTLA4Ig, and infusional AEs occurring within 1 hour of the start of CTLA4Ig infusion were reported for only 1 subject. The clinical laboratory data for hematology and blood chemistry were generally unremarkable and no safety issues were identified. Four (4) subjects became seropositive for anti-CTLA4-T antibodies at Month 12, 2 of which tested positive for neutralizing antibodies. The development of antibodies did not appear to be correlated with clinical safety findings.

The inventors discovered that administration of CTLA4Ig retarded progression to definite RA in patients with UA. Additionally, the disease-modifying effects of CTLA4Ig treatment were maintained for 6 months after therapy was stopped.

The invention will be more fully understood by reference to the following examples. They should not, however, be construed as limiting the scope of the invention. All citations throughout the disclosure are hereby expressly incorporated by reference.

EXAMPLE I

CTLA4Ig, lyophilized, (250 mg/vial) drug product is a sterile, non-pyrogenic lyophile suitable for intravenous (IV) administration. Each single-use vial contains 250 mg of CTLA4Ig which is constituted with Sterile Water for Injection, USP and further diluted with 0.9% Sodium Chloride Injection, USP, at the time of use.

The batch formula for a 115 liter batch size is described in Table 5 below.

TABLE 5

Batch Formula

| Component | Amount (kg) |
|---|---|
| CTLA4Ig drug substance[a] | 4.6 |
| Maltose monohydrate | 9.2 |
| Hydrochloric Acid | Adjust to pH 7.5 |
| Sodium hydroxide | Adjust to pH 7.5 |
| Water for Injection | q.s. to 119.6[b] |

[a]CTLA4Ig drug substance: protein concentration 50 mg/ml, 25 mM phosphate, 50 mM sodium chloride, pH of 7.5, <5% HMW species.
[b]Formulated bulk solution density = approx. 1.04 g/ml.

The required quantity of CTLA4Ig drug substance is added to a cleaned and sterilized stainless steel compounding vessel equipped with a mixer. The drug substance solution is mixed at 250±50 rpm while maintaining the solution temperature between 5°-25° C.

The required quantity of maltose monohydrate powder is added to the compounding vessel. The solution is mixed for a minimum of 10 minutes at 15°-25° C.

The solution pH is adjusted to 7.3-7.7, if necessary using the previously prepared 1 N sodium hydroxide solution or 1 N hydrochloric acid solution. The batch is brought to the final batch weight (final q.s.) using Water for Injection, USP, and mixed for a minimum of 8 minutes. The formulated bulk solution is sampled for pH.

Formulated Bulk Solution is pre-filtered with one 0.45-µm filter. The formulated bulk solution after 0.45-µm filter is sampled for bioburden and bacterial endotoxin (BET).

The pre-filtered formulated bulk Solution is sterile filtered with two 0.22-µm filters in series prior to filling.

Sterile filtered Formulated Bulk Solution is filled and partially stoppered with a 20 nm-Daikyo gray butyl stopper by a fully automatic filling/stoppering machine. The 15-cc Type I flint tubing glass vials are washed and sterilized/depyrogenated.

The filled and partially stoppered drug product vials are lyophilized. A summary of the freeze drying cycle used during lyophilization of CTLA4Ig drug product is provided in Table 6 below.

TABLE 6

Freeze Dry Cycle for CTLA4Ig Lyophilized Drug Product

| Process parameter | In-process control |
|---|---|
| Loading Temperature | 5 ± 3° C. |
| Freezing (Shelf Ramp) | From 5° C. to −45° C. in 2.5 hr. |
| Freezing | Hold at −45 ± 3° C. for 4 hr. |
| Primary Drying (Shelf Ramp) | From −45° C. to −19° C. in 2 hr. |
| Primary Drying (Vacuum) | 100 ± 20 microns |
| Primary Drying | Hold at −19 ± 2° C. for 84 hr. |
| Intermediate Drying (Shelf Ramp) | From −19° C. to 0° C. in 2 hr. |
| Intermediate Drying | Hold at 0 ± 3° C. for 8 hr. |
| Secondary Drying (Shelf Ramp) | From 0° C. to 30° C. in 2.5 hr. |
| Secondary Drying (Vacuum) | 100 ± 20 microns |
| Secondary Drying | Hold at 30° C. for 12 hr. |
| Stoppering | 30 ± 3° C. |
| Stoppering (Vacuum) | 500 ± 100 microns |
| Storage Before Unloading | Hold at 20 ± 3° C. for at least 4 hr. |

At the end of the lyophilization cycle, the chamber pressure is raised to 500 microns using sterile filtered nitrogen and vial stoppering is performed under vacuum. The stoppered vials remain inside the lyophilizer for at least 4 hours. The lyophilized and stoppered vials are sealed with a 20-mm aluminum, white flip-off seal under HEPA filtered air by the capping machine. The sealed vials are rinsed with deionized water by an exterior vial washer. The washed drug product vials are stored at 2 to 8° C.

The composition of lyophilized CTLA4Ig (250 mg/vial) drug product is listed in Table 7 below.

TABLE 7

Composition of Lyophilized CTLA4Ig (250 mg/vial) Drug Product

| Component | Amount (mg/vial)[b] |
|---|---|
| CTLA4Ig | 262.5 |
| Maltose monohydrate | 525 |
| Sodium phosphate monobasic, monohydrate[b] | 18.1 |

TABLE 7-continued

Composition of Lyophilized CTLA4Ig (250 mg/vial) Drug Product

| Component | Amount (mg/vial)[b] |
|---|---|
| Sodium chloride[b] | 15.3 |
| Hydrochloric Acid | Adjust to 7.5 |
| Sodium hydroxide | Adjust to 7.5 |

[a]Includes a 5% overfill for vial, needle, syringe loss.
[b]These components are present in the CTLA4Ig drug substance solution.

EXAMPLE II

CTLA4Ig SC, 125 mg/ml (125 mg/vial) drug product is formulated as a sterile, non-pyrogenic ready-to-use solution suitable for subcutaneous administration. A batch of CTLA4Ig SC, 125 mg/ml (125 mg/vial) drug product is manufactured at 5-L scale (3,500 vials). The batch formula is described in Table 8 below.

TABLE 8

Batch Formula

| Component | Amount (gm) |
|---|---|
| CTLA4Ig drug substance[a] | 625 |
| Sucrose | 850 |
| Poloxamer 188 | 40 |
| Sodium phosphate monobasic, monohydrate | 0.715 |
| Sodium phosphate dibasic, anhydrous | 4.86 |
| Water for Injection | q.s. to 5.0 L |
| Total Batch size (L) | 5.0 |

[a]CTLA4Ig drug substance: protein concentration 50 mg/ml, 25 mM sodium phosphate, 50 mM sodium chloride, pH of 7.5, <5% HMW species.

As described above in Example I, the manufacturing process for CTLA4Ig SC, 125 mg/ml (125 mg/vial) drug product involves buffer exchange of the bulk drug substance from 25 mM sodium phosphate, 50 mM sodium chloride at a pH of 7.5 to 10 mM sodium phosphate pH 7.8 buffer, followed by concentration of the protein from ~50 mg/ml to ~150 mg/ml by removal of buffer. Sucrose and Poloxamer 188 are then dissolved in the concentrated protein solution and final batch weight is adjusted with 10 mM sodium phosphate buffer, pH 7.8. The bulk solution is filtered through 0.22 micron sterilizing filter and filled into sterilized and depyrogenated 5-cc Type I flint glass vials, stoppered with 20 mm rubber stoppers and sealed with 20 mm aluminum flip-off seals.

The composition of CTLA4Ig SC drug product, 125 mg/ml (125 mg/vial) is provided in Table 9 below.

TABLE 9

Composition of CTLA4Ig SC, 125 mg/ml (125 mg/vial) Drug Product

| Component | Amount (mg/vial)[c] |
|---|---|
| CTLA4Ig | 175 |
| Sucrose | 238 |
| Poloxamer 188 | 11.2 |
| Sodium phosphate monobasic, monohydrate | 0.20 |
| Sodium phosphate dibasic, anhydrous | 1.36 |
| Water for Injection | q.s. to 1.4 ml |

[c]Includes 40% overfill for Vial, Needle, Syringe loss.

EXAMPLE III

Rheumatoid arthritis (RA) is an auto-immune disorder which can lead to progressive joint destruction, deformity, significant physical disability, and poor quality of life. No therapy has been demonstrated to prevent the development of RA. This study will compare the efficacy of CTLA4Ig with placebo in preventing the development of RA in subjects with recent onset undifferentiated arthritis (UA) who are at high risk for the development of RA during the period of the study.

Primary Objective

To assess the proportion of subjects with UA who develop RA as defined by 1987 ARA criteria one year after the start of blinded study medication.

Secondary Objectives

1) To assess the proportion of subjects with UA who develop RA as defined by 1987 ARA criteria two years after the start of blinded study medication.

2) To assess the degree of synovitis and structural joint damage of the hands (carpal, MCP and PIP joints) at 6, 12, and 24 months after the start of study therapy between the two treatment groups using MRI imaging.

3) To assess the proportion of subjects with persistent symptomatic clinical synovitis at 6, 12, and 24 months after the start of medication between the two treatment groups.

4) To assess the pharmacodynamic effect of CTLA4Ig on serum levels of autoantibodies [IgM rheumatoid factor and anti-cyclic citrullinated peptide (anti-CCP2)].

5) To assess disease activity over time between the treatment groups using the mean values of the full DAS (CRP) score.

6) To assess the proportion of subjects with a full DAS score of <1.6 at 6, 12, and 24 months.

7) To assess physical function and health-related quality of life using the Disability Index of HAQ (HAQ) and SF-36 instruments, respectively.

8) To assess the safety of CTLA4Ig in this study population, including evaluation of the immunogenicity of CTLA4Ig following completion of a six-month course of treatment.

Tertiary Objective

1) To assess changes in core components of the ACR RA (American College of Rheumatology Rheumatoid Arthritis) composite variable over time between the two treatment groups.

Study Design

This is a randomized, double-blind, placebo-controlled, two-arm parallel design study of 12 months duration to the primary endpoint and 24 months to secondary endpoint. Subjects will be randomized 1:1 to receive either CTLA4Ig or placebo for the first six months of the study. Randomization will be stratified into two groups based on the presence or absence of erosions (read centrally). Subjects will be allowed to take non-steroidal anti-inflammatory drugs (NSAIDs) throughout the study. Subjects will be allowed to take a stable low dose oral corticosteroid (equivalent to ≦10 mg prednisone daily) throughout the study. Up to two of the following high dose corticosteroid concomitant medications may be utilized every six months of the trial at the discretion of the investigator: oral course (equivalent to 20 mg/day prednisone daily for a maximum of two weeks), or a single IM dose or a single IA dose. Subjects with persistent arthritis after six months of study medication but who do not meet the criteria for RA will be observed off of study medication and will be allowed to take the concomitant medications described above at the discretion of the investigator. No subsequent dosing with study medication will be allowed.

Subjects who develop the primary endpoint (RA by ARA criteria) at any point during the trial will be discontinued from the study and allowed to receive anti-rheumatic therapy at the discretion of the investigator, including DMARDs and/or biologic therapy.

Subjects will be initially dosed based on their weight at the screening visit. Subjects weighing <60 kg will receive 500 mg; subjects weighing between 60 to 100 kg will receive 750 mg, and subjects weighing >100 kg will receive 1 gram. CTLA4Ig will be administered on Days 1, 15, 29 and every 28 days thereafter for a total of 8 doses. Subject will be allowed to take a stable low doses oral corticosteroid (equivalent to $\leq$10 mg prednisone daily) throughout the study.

Subjects who have been diagnosed with undifferentiated inflammatory arthritis will be evaluated in the Screening Period for the presence or absence of antibodies against cyclic citrullinated peptides (anti-CCP2). Subjects who have a positive anti-CCP2 test will be stratified based on the presence or absence of erosions and randomized into the Study Drug Treatment Period. The Study Drug Treatment Period will be six months of treatment with either CTLA4Ig or placebo. Subjects completing the treatment period who do not meet the criteria for RA will be observed off of study medication in the Observation Period with the blind maintained. The Observation Period will consist of quarterly visits for 18 months for safety and efficacy.

Study Population

Men or women (not nursing and not pregnant) at least 18 years of age but no greater than 75 years old with a diagnosis of undifferentiated inflammatory arthritis (UA) who have symptomatic clinical synovitis of two or more joints and who 1) possess at least one and not more than three of the 1987 ARA criteria for the diagnosis of RA, 2) do not meet diagnostic criteria for any other rheumatic disease (e.g., lupus erythematous), and 3) who are also positive for autoantibodies against cyclic citrullinated peptides by ELISA (Immunoscan RA Mark 2, Euro-Diagnostica, Arnhem, The Netherlands). Disease duration [defined as the time from the onset of symptoms (joint pain, swelling, or significant stiffness) of undifferentiated inflammatory arthritis to enrollment] must be less than 18 months. No prior therapy with DMARD or biologic therapy is allowed before screening.

Criteria for Evaluation

The primary outcome of the study will be the proportion of subjects with a diagnosis of RA by 1987 ARA criteria at 12 months.

Secondary efficacy outcome measures include the proportion of subjects with a diagnosis of RA by 1987 ARA criteria at 24 months, the proportion of subjects with persistent symptomatic clinical synovitis at 6, 12, and 24 months, the mean full DAS (CRP) score at 6, 12, and 24 months, the proportion of subjects with a DAS score of <1.6 at 6, 12, and 24 months, titers of rheumatoid factor and anti-CCP antibodies and inflammation and structural damage (the degree of synovitis, erosions, and osteitis) of the hands by gadolinium MRI using a centralized reader blinded to sequence and treatment. Subject reported outcomes will include the HAQ and SF-36.

The changes in core components of the ACR RA composite variable will be assessed over time between the two treatment groups as a tertiary objective.

Efficacy Analyses

The primary efficacy analysis will be to assess the rates for development of RA at 12 months in CTLA4Ig and placebo. Point and interval estimates for the proportion of subjects with a diagnosis of RA at 12 months for the two treatment groups will be provided. Subjects who discontinue from the study with a stated reason of "lack of efficacy" in the CRF will be considered as a non-responder for the primary endpoint (i.e., they will be counted in the numerator and denominator while assessing the proportion of subjects who develop RA by the ARA criteria). If a subject has missing data at the Month 12 visit not due to discontinuation and an evaluation from the subsequent visit, this evaluation will be used in the 12 month analysis. Otherwise, subjects will not be included in the analysis. Similar analyses will be performed for assessing rates for RA development at 24 months.

The degree of synovitis and structural joint damage will be assessed using MRI imaging. The OMERACT 6 RA MRI scoring system will be used (Ostergaard, M. et al., "OMERACT Rheumatoid Arthritis Magnetic Resonance Imaging Studies. Core Set of MRI Acquisitions, Joint Pathology Definitions, and the OMERACT RA-MRI Scoring System", *J. Rheumatology*, 30(6):1385-1386 (2003)). Changes from baseline in the erosion, edema, and synovitis will be summarized at 6, 12, and 24 months using descriptive statistics.

The persistence of symptomatic clinical synovitis will be assessed at 6, 12 and 24 months. The rates for persistent synovitis will be summarized with point estimates and 95% confidence intervals for the CTLA4Ig and placebo groups.

The pharmacodynamic effect of CTLA4Ig on serum levels of autoantibodies [IgM rheumatoid factor and anti-cyclic citrullinated peptide (anti-CCP2)] will be assessed. The distribution of the pharmacodynamic variables at baseline, month 12 and month 24 visits, along with their changes from baseline, will be summarized by treatment group. The proportion of subjects reaching positive/negative results will be summarized by treatment arm and the baseline status (positive/negative).

Mean changes from baseline in full DAS (CRP), HAQ and all components of SF-36 at 6, 12 and 24 months will be summarized with point estimates and 95% confidence intervals for the CTLA4Ig and placebo groups in each visit. In addition, percentages of subjects with remission (full DAS score <1.6) will be summarized by treatment arm.

The changes in core components of the ACR RA composite variable will be assessed over time between the two treatment groups.

Safety Analyses

Significant physical examination findings and clinical and laboratory test results will be listed Summary statistics will be tabulated. Frequency distributions and individual listings of all adverse events will be generated. Changes in clinical laboratory test results from baseline will be listed. Discontinuations by cause will be summarized by treatment arm.

Immunogenicity Analysis

The distribution of immunogenicity variables and their changes from baseline will be summarized using descriptive statistics (geometric means, standard deviations, etc.) and 95% confidence intervals of the changes from baseline will also be calculated. Lack of immunogenicity is defined as the absence of a positive response. The existence of a positive response is defined based on an assay cut-off value for positivity for each assay and further confirmation of that response by immunodepletion. For the anti-CTLA4Ig assay, the value is calculated by dividing the mean post-dose subject serum sample OD by the mean of its corresponding predose (Day 1) subject serum sample OD. For the anti-CTLA4-T assay, the cut-off value is calculated by dividing the mean subject serum sample OD by the mean OD of the negative control on the sample plate. The cut-off value is established during the assay validation and may be re-established when changes are made in the subject populations or assay reagents. If a sample is negative, it is assigned a value of < the dilution evaluated. If the value is positive, a serial dilution is evaluated and it is assigned a titer value corresponding to the reciprocal of the interpolated serum dilution that is equal to the established cut-off value for positivity. Rate of positive response (if any) and its 95% confidence interval will also be calculated.

Subject Selection Criteria

For entry into the study, the following criteria MUST be met.

Inclusion Criteria

A. Signed Written Informed Consent

Subject is willing to participate in the study and signed the informed consent.

B. Target Population

Subjects must have a diagnosis of UA. A subject with UA should have symptomatic clinical synovitis of two or more joints and should possess at least one and not more than three of the criteria for classification of RA of the American Rheumatism Association (1987).

Subjects must not meet diagnostic criteria for any other rheumatic disease (e.g., lupus erythematous).

The subject's disease duration [defined as the time from the onset of symptoms (joint pain, swelling, or stiffness) of arthritis to enrollment must be less than 18 months.

Subjects must have be positive for autoantibodies against cyclic citrullinated peptides by ELISA (Immunoscan RA Mark 2, Euro-Diagnostica, Anthem, The Netherlands).

C. Age and Sex

Men and women, ages 18-75 years old. Men and Women of childbearing potential are eligible if they are practicing effective contraceptive measures.

D. Concomitant Medication

Use of a stable low dose oral corticosteroid is allowed throughout the study. Treatment must have been reduced to the equivalent of $\leq$10 mg prednisone daily for 28 days and stabilized for at least 25 out of the 28 days prior to treatment (Day 1).

Exclusion Criteria

A. Sex and Reproductive Status

1) WOCBP who are unwilling or unable to use an acceptable method to avoid pregnancy for the entire study period and for up to 10 weeks after the last infusion of CTLA4Ig 2) Women who are pregnant or breastfeeding 3) Women with a positive pregnancy test on enrollment or prior to study drug administration 4) Males unwilling or unable to use an adequate method of contraception for the entire study drug treatment period and for up to 10 weeks after the last infusion of study medication.

B. Medical History and Concurrent Diseases

5) Subjects who are impaired, incapacitated, or incapable of completing study related assessments.

6) Subjects who meet diagnostic criteria for any other rheumatic disease (e.g., lupus erythematous).

7) Undifferentiated Arthritis duration of greater than 18 months

8) Subjects who have previously received treatment with an approved biologic RA therapy (infliximab, etanercept, anakinra, adalimumab).

9) Subjects with active vasculitis of a major organ system.

10) Current symptoms of severe, progressive, or uncontrolled renal, hepatic, hematological, gastrointestinal, pulmonary, cardiac, neurological, or cerebral disease. Concomitant medical conditions that, in the opinion of the investigator, might place the subject at unacceptable risk for participation in this study.

11) Female subjects, who have not had age and/or risk factor appropriate breast cancer screening (as defined by published guidelines and/or local standards endorsed by the national cancer or medical society and/or the Ministry of Health), or who have had a breast cancer screening study that is suspicious for malignancy, and in whom the possibility of malignancy cannot be reasonably excluded following additional clinical, laboratory or other diagnostic evaluations.

12) Subjects with a history of cancer within the last five years (other than non-melanoma skin cell cancers cured by local resection). Existing non-melanoma skin cell cancers must be removed prior to dosing.

13) Subjects who have clinically significant drug or alcohol abuse.

14) Subjects with any serious acute bacterial infection (such as pneumonia or pyelonephritis unless treated and completely resolved with antibiotics).

15) Subjects with severe chronic or recurrent bacterial infections (such as recurrent pneumonia, chronic bronchiectasis).

16) Subjects with active tuberculosis (TB) requiring treatment within the previous 3 years. Subjects with a positive PPD at screening will not be eligible for the study unless active TB infection has been ruled out, and they have a negative chest x-ray at enrollment. A PPD response that is equal to or greater than 10 mm should be considered a positive test, although a lower threshold (5 mm) may be applied as determined by the clinical circumstance and investigator according to published guidelines and/or local standards endorsed by the medical society.

17) Subjects with herpes zoster that resolved less than 2 months prior to enrollment.

18) Subjects with evidence (as assessed by the investigator) of active or latent bacterial or viral infections at the time of potential enrollment, including subjects with evidence of Human Immunodeficiency Virus (HIV) infection.

C. Physical and Laboratory Test Findings

19) Hepatitis B surface antigen-positive subjects.

20) Hepatitis C antibody-positive subjects who are also RIBA-positive or PCR-positive.

21) Subjects with any of the following laboratory values:

Hgb<8.5 g/dL.

WBC<3,000/mm3 ($3\times10^9$/L)

Platelets<100,000/mm3 ($100\times10^9$/L).

Serum creatinine>2 times upper limit of normal.

Serum ALT or AST>2 times upper limit of normal.

Any other laboratory test results that, in the opinion of the investigator, might place the subject at unacceptable risk for participation in this study.

D. Prohibited Therapies and/or Medications

22) Subjects who have at any time received treatment with CTLA4Ig, or CTLA4Ig.

23) Subjects who have received treatment with any investigational drug within 28 days (or less than 5 terminal half-lives of elimination) of the Day 1 dose.

24) Subjects currently receiving treatment with immunoadsorption columns (such as Prosorba columns), mycophenolate mofetil (CELLCEPT®), cyclosporine, D-Penicillamine, or calcineurin inhibitors.

25) Prior treatment with DMARD before screening.

E. Other Exclusion Criteria

26) Prisoners or subjects who are compulsorily detained (involuntarily incarcerated) for treatment of either a psychiatric or physical (e.g., infectious disease) illness must not be enrolled into this study.

Subjects Participating in the MM Evaluation

The radiologist at the site's MM facility is responsible for determining if a subject is contraindicated from having this procedure. The following is a list of some common conditions that may preclude the subject from having MRI of the hands/wrists. However, this should not be used as a substitute for local clinical standards of care. The ultimate decision to perform MRI in an individual subject in this study rests with the site radiologist, the investigator, and the standard set by the local Ethics Committee.

1) Subjects who have a history of claustrophobia.
2) Subjects who have a physical limitation related to fitting in the bore of the magnet (i.e., body weight in excess of 250 pounds or 113.4 kilograms).
3) Subjects with tattooed eye-liner or tattoos directly on the hand or wrist (area to be imaged).
4) Subjects who have a history of allergic reaction to contrast agents.
5) Subjects who had exposure to a radiological contrast agent within the 72 hours prior to the MM examination.
6) Subjects who have a fused joint in the wrist or joint replacements in the hand or wrist that are being evaluated by the MRI examination.
7) Subjects with a pacemaker, epicardial pacemaker wires, MRI-incompatible cardiac valve prostheses, MRI-incompatible vascular clips less than two-month old, or MM-incompatible aneurysm clips of any age.
8) Subjects with MM-incompatible cochlear implants.
9) Subjects with spinal nerve stimulators.
10) Subjects with an infusion pump.
11) Subjects with metallic fragments in the eyes/orbits or in the vicinity of the brain or major neurovascular structures of the body, subjects with an employment history which involves exposure to welding, or subjects who have shrapnel any place in their body.

Administration of CTLA4Ig or Placebo

Subjects will be randomized to 1 of 2 treatment groups:
Group 1: CTLA4Ig intravenous infusions (N=25).
Group 2: Placebo intravenous infusions (N=25).

Subjects receiving active CTLA4Ig will be dosed based on their screening visit weight. Subjects weighing <60 kg will receive 500 mg, subjects weighing 60 to 100 kg will receive 750 mg, and subjects weighing >100 kg will receive 1 gram. Subjects who are randomized to receive placebo will be given Dextrose 5% in Water or Normal Saline (NS).

Infusion doses will be based upon the subject's body weight from the screening visit immediately prior to Day 1 visit. The Central. Randomization System will confirm the subject's body weight and assign the number of vials of CTLA4Ig to allocate for the visit. Subjects will receive doses of study medication at every treatment period visit (Days 1, 15, 29, 57, 85, 113, 141, and 169). A +/−3 day window is allowed for doses on Days 15 and 29; a +/−7 day window is allowed for doses thereafter. Infusions should occur at approximately the same time of day throughout the duration of the study. All doses of study medication will be administered intravenously in a fixed volume of 100 ml at a constant rate of flow over approximately 30 minutes. The IV line must be flushed with 25 ml of D5W or NS solution at the end of the infusion. The infusion solution must be supplied to personnel administering the dose in a container not identifying the contents so as to maintain the blind. The clinical assessor must remain blinded to treatment assignment by having a different qualified staff member perform the study medication infusion. All intravenous infusions will be with the subject in the seated position. No adjustments will be made in treatment dose level or schedule. Subjects will be observed for adverse events and vital signs (blood pressure, heart rate, respirations, temperature) will be monitored from the start of each infusion (pre-dose and 60 minutes). There is a +/−5-minute window for vital sign collection. Subjects will be observed for a minimum of 1 hour from the start of the infusion. The observation period should be extended if clinically indicated.

Dose Modifications in the Absence of Adverse Events

In the absence of adverse events deemed at least possibly related to study medication treatment, subjects will complete their scheduled infusions as prescribed by protocol. A subject's scheduled dosing may be administered within 72 hours (+/−3 days) prior to or after the target day to adjust for the subject's and/or the site personnel's convenience for Days 15 and 29. A +/−7 day window is allowed for doses thereafter.

Prohibited and Restricted Therapies During the Study

DMARDs (e.g., methotrexate, oral or parenteral gold, sulfasalazine, chloroquine, hydroxychloroquine, D-penicillamine, azathioprine, leflunomide, cyclosporine) or biologics (e.g., etanercept, adalimumab, anakinra) are not permitted.

Subjects will be allowed to take non-steroidal anti-inflammatory drugs throughout the study. Subjects will be allowed to take a stable low dose oral corticosteroid (equivalent to $\leq 10$ mg prednisone daily) throughout the study. Up to two of the following high dose corticosteroids may be utilized every six months of the trial at the discretion of the investigator: oral course (equivalent to 20 mg/day prednisone daily for a maximum of two weeks), or a single IM (intramuscular) dose or a single IA (intra-articular) dose.

Non-steroidal anti-inflammatory drug (NSAID), including aspirin (ASA), use is permitted during this period.

IA and IM injections of corticosteroids should be avoided. No IA or IM injections of high dose steroids ARE permitted within one month of the key efficacy evaluation (i.e., Days 169, Month 12, and Month 24).

The following medications may be used, except 12 hours before a joint evaluation:
acetaminophen (paracetamol)
combination products including acetaminophen and narcotic analgesics (e.g., acetaminophen with codeine phosphate, acetaminophen with propoxyphene napsylate, acetaminophen with oxycodone hydrochloride, acetaminophen with hydrocodone bitartrate, etc.) tramadol

TABLE 10

Study Procedures and Observations
A. Double-Blind Study Drug Treatment Phase

| Visit Day | Day 1[a] | Day 15 (+/−3 days) | Day 29 (+/−3 days) | Day 57 (+/−7 days) | Day 85 (+/−7 days) | Day 113 (+/−7 days) | Day 141 (+/−7 days) | Day 169 (+/−7 days) |
|---|---|---|---|---|---|---|---|---|
| Randomize & stratify subjects (Contact Central Randomization Center) | X | | | | | | | |
| Efficacy Assessments | | | | | | | | X |
| Radiographs of Hands and Feet | | | | | | | | X |

TABLE 10-continued

Study Procedures and Observations
A. Double-Blind Study Drug Treatment Phase

| Visit Day | Day 1[a] | Day 15 (+/−3 days) | Day 29 (+/−3 days) | Day 57 (+/−7 days) | Day 85 (+/−7 days) | Day 113 (+/−7 days) | Day 141 (+/−7 days) | Day 169 (+/−7 days) |
|---|---|---|---|---|---|---|---|---|
| Gadolinium MRI of Hand-Wrist (European sites only) | | | | | | | | X |
| Tender joint count[b] | X | X | X | X | X | X | X | X |
| Swollen joint count | X | X | X | X | X | X | X | X |
| Subject's assessment of pain | X | X | X | X | X | X | X | X |
| Subject's assessment of disease activity | X | X | X | X | X | X | X | X |
| Physician's global assessment of disease activity | X | X | X | X | X | X | X | X |
| Subject's assessment of physical function (HAQ) | X | X | X | X | X | X | X | X |
| SF-36 | X | | X | | X | | | X |
| Subjects response to therapy | | | | | X | | | X |
| Safety Assessments | | | | | | | | |
| Adverse Event Monitoring | X | X | X | X | X | X | X | X |
| Interim Physical Exam | X | X | X | X | X | X | X | X |
| ECG | | | | | | | | X |
| Vital Signs | X | X | X | X | X | X | X | X |
| Labs | | | | | | | | |
| CBC | X | X | X | X | X | X | X | X |
| Chemistry panel | X | X | X | X | X | X | X | X |
| Urinalysis | | | | | | | | X |
| Urine/serum pregnancy test (WOCBP only)[c] | X | X | X | X | X | X | X | X |
| CRP | X | X | X | X | X | X | X | X |
| IgM RF | X | | | | | | | X |
| Biomarkers (IL-6, TNFα, IL-1 beta, MMP-3) | X | | | | | | | X |
| HLA Typing | X | | | | | | | |
| Immunogenicity | X | | | | | | | X |
| Anti-CCP2 | | | | | | | | X |
| Dosing | X | X | X | X | X | X | X | X |

[a] All assessments and results must be reviewed prior to contacting the Central Randomization Center. All assessments must be performed prior to dosing.
[b] A 68/66 count assessment will be done.
[c] A negative pregnancy test should be done within 48 hours prior to the visit.

B. Post-Treatment Double-Blind Observation

| Visit Day (+/−7 days allowed for Months 9, 15, 18, and 21; +/−30 days allowed for Months 12 and 24) | Month 9 (Day 253) | Month 12 (Day 365)[a] | Month 15 (Day 449) | Month 18 (Day 533) | Month 21 (Day 617) | Month 24 (Day 729) | Early Term |
|---|---|---|---|---|---|---|---|
| Efficacy Assessments | | | | | | | |
| Radiographs of Hands and Feet[b] | | X | | | | X | |
| Gadolinium MRI of Hand-Wrist (European Sites only) | | X | | | | X | |
| Tender joint count[c] | X | X | X | X | X | X | X |
| Swollen joint count | X | X | X | X | X | X | X |
| Subject's assessment of pain | X | X | X | X | X | X | X |
| Subject's assessment of disease activity | X | X | X | X | X | X | X |
| Physician's global assessment of disease activity | X | X | X | X | X | X | X |

| B. Post-Treatment Double-Blind Observation | | | | | | | |
|---|---|---|---|---|---|---|---|
| Visit Day (+/−7 days allowed for Months 9, 15, 18, and 21; +/−30 days allowed for Months 12 and 24) | Month 9 (Day 253) | Month 12 (Day 365)[a] | Month 15 (Day 449) | Month 18 (Day 533) | Month 21 (Day 617) | Month 24 (Day 729) | Early Term |
| Subject's assessment of physical function (HAQ) | X | X | X | X | X | X | X |
| SF-36 | X | X | X | X | X | X | X |
| Subjects response to therapy | X | X | X | X | X | X | X |
| Safety Assessments | | | | | | | |
| Adverse event monitoring | X | X | X | X | X | X | X |
| Interim Physical Exam | X | X | X | X | X | X | X |
| Complete Physical Exam | | | | | | | |
| Weight | | | | | | X | X |
| Vital Signs | X | X | X | X | X | X | X |
| Labs | | | | | | | |
| CBC | X | X | X | X | X | X | X |
| Chemistry panel | X | X | X | X | X | X | X |
| Urinalysis | | | | | | X | X |
| Urine/serum pregnancy test (WOCBP only) | X[d] | X | X | X | X | X | X |
| Breast Cancer Screening Annual/Anniversary (women only) | | X | | | | X | X |
| CRP | X | X | X | X | X | X | X |
| IgM RF | | X | | | | X | |
| Biomarkers (IL-6, TNFα, IL-1 Beta, MMP-3) | | X | | | | X | |
| Immunogenicity | X | X | | | | | |
| Anti-CCP2 | | X | | | | X | |

[a] If the subject does not come to the clinic for the Month 12 visit, all the assessments required at Month 12 will be done at the next clinic visit.
[b] If radiographs are taken between Months 6 and 12 and the subject discontinues, the radiographs should be forwarded to the central reader for assessment of the Genant-modified Sharp score.
[c] A 68/66 count joint assessment will be done.
[d] A negative pregnancy test should be done within 48 hours prior to the visit.

Safety Assessments

All subjects who receive a dose of study drug will be evaluated for safety and immunogenicity testing. Safety outcomes include adverse events, clinically significant changes in vital signs, and laboratory test abnormalities. The Investigator will determine the severity of each adverse event to be mild, moderate, severe, or very severe. Laboratory findings which the Investigator feels are clinically relevant based on Laboratory Guidelines should be recorded as adverse events. In addition, the Investigator will determine the relationship of the adverse event to the administration of the study drug.

Complete and/or interim physical examinations may be performed by a Doctor of Medicine (MD), Doctor of Osteopathy (DO), Physician's Assistant (PA), or Nurse Practitioner (NP). While the interim physical exam may not be as comprehensive as the initial full examination, key aspects of the interim examination should evaluate important body systems as clinically indicated. These body systems can include lymph nodes, liver, spleen, and breast, at the discretion of the examiner. An interim physical examination may note any changes in the subject's condition (body systems) since the last assessment and does not preclude examination of any of the body systems as clinically indicated.

A chest x-ray at the screening visit is required if not already performed within six months of obtaining written informed consent or if documentation is not on file.

A 12-lead electrocardiogram (ECG) is required if not already performed within 6 months of obtaining written informed consent or if documentation is not on file. The ECG will be repeated at the end of the treatment period (Day 169) or 28 days after discontinuation if the subject terminates from the treatment period early.

To identify subjects with latent tuberculosis (TB), a PPD test (purified protein derivative tuberculin skin test) is required if not performed within six months of screening or if documentation of testing within six months is not on file. All subjects including those with prior BCG vaccination should be evaluated for latent TB.

PPD skin test should be performed in accordance to published guidelines that provide recommendations for PPD testing and interpretation in subjects with rheumatoid arthritis who are being considered for treatment with biologic agents ("Preliminary guidelines for diagnosing and treating tuberculosis in subjects with rheumatoid arthritis in immunosuppressive trials or being treated with biological agents", *Ann. Rheum. Dis.*, 61(Supp.):ii62-ii63 (2002) and Ex US sites, local guidelines endorsed by medical societies on PPD testing in subjects with RA being treated with biologics may also apply) subjects who are immunosuppressed ("Targeted Tuberculin Testing and Treatment of Latent Tuberculosis Infection", *Am. J. Respir. Crit. Care. Med.*, 161:S221-S247 (2000) and "Diagnostic Standards and Classification of Tuberculosis in Adults and Children", *Am. J. Respir. Crit. Care Med.*, 161:1376-1395 (2000)) and subjects with a prior history of BCG vaccinations.

Subjects with a positive PPD at screening will not be eligible for the study unless active TB infection has been ruled out and they have a negative chest x-ray at enrollment. A PPD response that is equal to or greater than 10 mm should be considered a positive test, although a lower threshold (5 mm) may be applied as determined by the clinical circumstance and investigator according to published guidelines and/or local standards endorsed by the medical society.

Before entry into this study female subjects are required to have age and/or risk-factor appropriate breast cancer screening. Breast cancer screening should be performed according to published guidelines and/or local standards endorsed by the National Cancer or Medical Society and/or the Ministry of Health. In addition, the breast cancer screening guidelines utilized by the investigational site should be made available to the local IRB/Ethics Committee and explained in the subject's informed consent.

Documented breast cancer screening performed within 6 months of screening will be accepted as meeting this requirement. However, screening will be required if documentation from the screening facility is not on file or a screening exam was performed more than 6 months prior to entry into study.

Based on study entry criteria for breast cancer screening, female subjects are required to have an annual or anniversary repeat breast cancer screening.

Plain radiographs of hands/wrists and feet should be taken at screening for eligible subjects. The radiographs conducted on eligible subjects (after confirmation of a positive anti-CCP2 test) will be sent to a central reader for assessment for the presence or absence of erosions. The information on erosions will be used for stratification into the study. Plain radiographs of hands/wrists and feet will also be taken at 6, 12, and 24 months and assessed by a central reader for the Genant-modified. Sharp score. If radiographs are taken between Months 6 and 12 and subject discontinued, the radiographs should be forwarded to the central reader for assessment.

A gadolinium MRI of the hand/wrist (one side of the body only) should be performed prior to randomization for all subjects at European sites only who have a positive anti-CCP2 test and symptomatic clinical synovitis of two more joints of the hand or wrist. The MRI will be assessed by a central reader. An follow-up MRI of the same hand/wrist will also be performed at 6, 12, and 24 months and assessed by a central reader. No MRI will be done of the feet.

Urine or serum pregnancy tests will be performed within 48 hours prior to each visit up for all WOCBP. If any female subject becomes pregnant, she will be immediately terminated from the study.

Gadolinium MRI of Hand and Wrist

A Gadolinium MRI study of the hand and wrist (one side only) will be performed in all subjects at European sites only who have a positive anti-CCP2 test and symptomatic clinical synovitis of two or more joints of the hand or wrist within two weeks prior to the first dose of study medication (Day −14 to Day −1) using a 1.5 Tesla machine and repeated at the 6, 12 and 24 months timepoint. The MR image data will be interpreted by radiologists at a central facility according to the OMERACT 6 method in the following manner:

Erosion/Edema Scoring in the Wrist and Hand

Erosions and bone marrow edema will be scored separately according to the OMERACT 6 grading scheme. Each bone in the wrist and hand (carpal bones, distal radius, distal ulna, metacarpal bases and the bones comprising the MCP joints) is scored separately on a 0-10 scale, as determined by the proportion of eroded bone and volume of edema (scored separately) compared to the assessed bone volume. The scoring scale is determined in 10% increments with a score of 10 representing >90% compromise of the assessed bone by erosions or edema.

Synovitis Scoring in the Wrist and Hand

Synovitis is assessed in multiple wrist regions (the distal radioulnar joint, the radiocarpal joint, the intercarpal and carpometacarpal joints as well as the 2nd-5th MCP joints) on a 0-3 scale. A score of 3 represents a severe grade with the volume of Gadolinium enhancing tissue comprising >⅔ of the assessed synovial compartment.

All MR images for all subjects with both baseline and 12 months image data available will be read by a trained central reader blinded to treatment allocation and to sequence.

HLA Typing

All subjects to be randomized will have peripheral blood drawn for HLA typing at Day 1 to determine the presence or absence of the alleles which are associated with RA susceptibility/severity (the "shared epitope" alleles HLA-DR0401 and 0404). Randomized subjects will be categorized as null, heterozygous, homozygous, or doubly heterozygous for these alleles. This information will further characterize the study subjects' risk for development of severe RA.

Laboratory Test Assessments

Blood and/or urine samples will be obtained prior to infusion at all visits from each subject entered in this study. Any laboratory test result that the Investigator considers clinically relevant should be recorded on the appropriate Adverse Event page of the CRF.

A. Hematology

Hemoglobin Hematocrit Total WBC count, including differential Platelet count RBC B. Blood Chemistry Sodium Creatinine Potassium Blood urea nitrogen (BUN) Chloride Total bilirubin Total Protein Alanine aminotransferase (ALT) Albumin Aspartate aminotransferase (AST) Calcium Gamma-glutamyltransferase (GGT) Phosphorus Alkaline phosphatase Uric Acid Glucose C. Urinalysis pH Protein Glucose Blood Microscopic examination of the urine sediment if blood, protein or glucose is positive on the dipstick.

D. Hepatitis Screen (performed at screening visit only) Hepatitis B surface antigen (if positive, core antibody) Hepatitis C antibody (if positive, RIBA or PCR)

E. Pregnancy Tests

Urine or serum pregnancy tests (minimum sensitivity 25 IU/L of HCG) must be performed for all WOCBP within 48 hours prior to each visit until the Month 9 visit. If any female subject becomes pregnant, she will be terminated from the study. Pregnancy tests will be processed locally.

F. Pharmacodynamic (PD) Tests

IgM RFC-reactive Protein (CRP) Inflammatory cytokines (IL-6, TNFα, IL-1 beta) Matrix Metalloproteinase 3 (MMP-3) Anti-CCP2

G. Immunogenicity Determination

Anti-CTLA4Ig antibody

H. Other

Human Leukocyte Antigens (HLA)

In addition, the investigator will obtain samples for additional laboratory tests if deemed necessary for monitoring subject safety.

Immunogenicity

The immunogenic potential of CTLA4Ig will be assessed based on levels of anti-CTLA4Ig antibodies.

Subjects who complete the study drug treatment phase will have serum samples obtained at visit Days 1, 169, 253 and Day 365 to be assayed for the presence of anti-CTLA4Ig antibodies.

Subjects who do not complete the study drug treatment phase of the study will have a serum sample collected: at Day 1 and at Days 28, 56 and 85 after the last dose of study medication. Samples will be assayed for the presence of anti-CTLA4Ig antibodies.

Validated sensitive, enzyme linked immunosorbent assay (ELISA) methods will be used to measure titers of both anti-CTLA4Ig antibodies in serum and anti CCP-2 in serum.

Efficacy Assessments

A. X-Rays of Hands and Feet

X-rays of hands and feet will be performed on all subjects with a positive anti-CCP2 test at Screening, Day 169, Month 12, and Month 24. All centers will need to meet technical requirements. Radiography of the hands and feet will be standardized to ensure sufficient image quality for the evaluation of radiographic progression of rheumatoid arthritis. Radiology facilities and personnel will be qualified for participation in the trial based on the technical capabilities of the equipment and experience and licensing of the x-ray technologists. Radiographic technique will be harmonized through the use of a written radiographic procedure manual and training of x-ray technologists. In addition the film-screen system will be standardized to ensure sufficient resolution for the evaluation of erosions and joint space narrowing. Radiographs collected for the trial will be sent to a central reading facility for quality control and central evaluation (in a blinded manner) by a radiologist trained and experienced in the scoring of rheumatoid arthritis by the Genant-modified Sharp grading scheme. A primary reader and backup reader will be assigned. The readers will be certified for the study through the evaluation of a set of test cases and evaluation of agreement between the readers. Readers will be blinded to the order of timepoints.

B. Gadolinium-Enhanced MRI of Hand-Wrist

A gadolinium-enhanced MRI of the hand-wrist will be performed on all randomized subjects with a positive anti-CCP2 test who have symptomatic clinical synovitis of the hands at screening, Day 169, Month 12, and Month 24. The subject's hand-wrist with more synovitis by clinical assessment should be selected initially and utilized for all subsequent evaluations. The baseline MRI (and all follow-up MRI studies) should not be performed if the and/wrist is asymptomatic or if there is no synovitis by clinical assessment.

The MRI examination will be standardized to ensure sufficient image quality for the evaluation of radiographic progression of rheumatoid arthritis. Radiology facilities and personnel will be qualified for participation in the trial based on the technical capabilities of the equipment and experience and licensing of the technologists. Radiographic technique will be harmonized through the use of a written radiographic procedure manual and training of technologists. MRI data collected for the trial will be sent to a central reading facility for quality control and central evaluation. Efficacy assessments will be performed only by the central reader.

C. Joint Count Assessments

The response measures will be reviewed and discussed with the investigational staff at the Investigator Meeting or other forum as a method of standardizing the grading between the investigational staff. The training and instruction on joint count assessment will be discussed at the Investigator's Meeting or at workshops.

Joint count assessments may be performed by the following personnel: MD, DO, PA, NP or RN. Ideally, the joint count should be performed before any other assessment or procedure is performed.

Every effort must be made to ensure the same evaluator(s) will complete the assessment for each subject. Visits should be scheduled with the availability of the evaluator(s) taken into account. If the evaluator(s) is unable to complete the evaluation, then a qualified individual, with overlapping experience may perform the evaluation. Documentation of who performed the evaluation is to be recorded in source notes.

D. Clinical Assessments

Clinical assessments of response should be performed by the same assessor(s) and at approximately the same time of day throughout the duration of the study. The clinical assessor(s) should be a different person from the one administering the study medication infusion.

Clinical assessors will complete the global assessments and joint count pages of the CRFs in their own handwriting. These pages will be source documents for the study.

Subjects will complete the HAQ and SF-36 pages of the CRF in their own handwriting. These pages will be source documents for this study.

The CRP obtained from the central laboratory will be utilized to calculate the full DAS.

E. Pharmacodynamic Assessments

Pharmacodynamic data collected in this study will include laboratory values consisting of continuous variables. Biomarkers for immunomodulation or inflammation in rheumatoid arthritis, including IgM RF, CRP, and anti-CCP2, will be collected.

CRP will be collected at each visit during the double-blind study drug treatment phase, the post-treatment double blind observation phase, as well as Early Termination in both phases.

Rheumatoid factor (IgM RF) and biomarkers will be collected at Day −21, Day 1, Day 169, and Months 12 and 24.

Anti-CCP2 will be collected at screening, Day 169, Month 12, and Month 24.

Additionally, a portion of the sera collected at each visit will be stored and the following biomarkers will be analyzed: pro-inflammatory cytokines TNFα, and IL-1 beta) and the matrix metalloproteinase 3 (MMP-3).

Outcomes Research Assessments

A. Physical Function

Physical function will be evaluated using the disability section of the full Health Assessment Questionnaire (HAQ) (Fries, J. F. et al., "Measurement of Subject Outcome in Arthritis", *Arthritis Rheum.*, 23:137-145 (1980)). This section includes 20 questions to assess physical functions in 8 domains: dressing, arising, eating, walking, hygiene, reach, grip and common activities. The questions are evaluated on a 4-point scale: 0=without any difficulty, 1=with some difficulty, 2=with much difficulty, and 3=unable to do. Higher scores indicate greater dysfunction. A disability index will be calculated by summing the worst scores in each domain and dividing by the number of domains answered.

B. Health-Related Quality of Life

The SF-36 will be used to measure health-related quality of life (Birrell, F. N. et al., "How does the Short Form 36 Health Questionnaire (SF-36) in Rheumatoid Arthritis (RA) Relate to RA Outcome Measures and SF-36 Population Values? A Cross-Sectional Study", *Clin. Rheumatol.*, 19:195-199 (2000); Keller, S. D. et al., "The SF-36 Arthritis-Specific Health Index (ASHI): IL Tests of validity in four clinical trials", *Med. Care*, 37(5 Suppl.):MS51-60 (May 1999); Ware, J. F. et al., "The SF-36 Arthritis-Specific Health Index (ASHI): I. Development and cross-validation of scoring algorithms", *Med. Care,* 37(5 Suppl.):MS40-50 (May 1999); and Kosinski, M. et al., "The SF-36 Health Survey as a generic outcome measure in clinical trials of subjects with osteoarthritis and rheumatoid arthritis: relative validity of scales in relation to clinical measures of arthritis severity", *Med. Care,* 37(5 Suppl.):MS23-39 (May 1999)). Individual subscale scores and two summary scores will be calculated: (1) physical component summary (PCS) which includes physical functioning, role-physical, bodily pain, and general health; (2) mental component summary (MCS) which includes vitality, social functioning, role-emotional, and mental health. The SF-36 was recommended by the FDA as a validated instrument to measure health-related quality of life in RA subjects (*Guidance for Industry, Clinical Development Programs for Drugs, Devices, and Biological Products for the Treatment of Rheumatoid Arthritis (RA)*, U.S. Department of Health and Human Services, Food and Drug Evaluation and Research (February 1999)).

Drug Product Information

A pharmacist or qualified personnel at the site, not otherwise associated with the conduct of the study, will reconstitute the drug for intravenous (IV) administration.

All reconstitution and dilutions must be performed using polypropylene non-siliconized syringes (Norm-Ject manufactured by Henke Sass Wolf in Germany.

NOTE: A separate needle and syringe MUST be used for each vial reconstituted.

Vials are sealed under vacuum. If any vials are found without this vacuum, they should be segregated and not used. These vials must be retained until reconciliation by your Study Drug Monitor.

NOTE: The vial should NOT be vented prior to reconstitution. To avoid foam formation following the addition of SWFI, the vial should be gently swirled until the contents are completely dissolved. Upon complete dissolution of the lyophilized powder, the vial should then be vented with a needle to dissipate any foam that may be present.

Each vial of CTLA4Ig drug product for Injection, 250 mg/vial, should be reconstituted with 10 mL of SWFI (without bacteriostatic agent) to yield a concentration of 25 mg/mL. In order to minimize foaming, the stream of SWFI should be directed to the sides of vial.

A sufficient excess of CTLA4Ig drug product is incorporated into each vial to account for withdrawal losses so that 10 mL of the reconstituted solution containing 250 mg can be withdrawn for parenteral administration. After reconstitution of the product the solution must be diluted further with D5W or 0.9% Sodium Chloride (NS="Normal" saline).

The continuous infusion solution must be filtered upon administration using an in-line, sterile, non-pyrogenic, low protein-binding filter with a pore size of 1.2 µm. This infusion should be administered over a period of approximately 30 minutes. Any unused portion of the infusion solution should not be stored for reuse.

No data is available on the compatibility of CTLA4Ig drug product with other intravenous substances. CTLA4Ig drug product should be administered in a separate intravenous line whenever possible and not mixed with other medications. Assure adequate and appropriate flushing between any other drug substances if other drugs are administered through the same line sequentially.

No incompatibilities have been observed with glass bottles or polyvinyl chloride bags and administration sets.

Care must be taken to assure sterility of the prepared solution, as the drug product does NOT contain any antimicrobial preservatives or bacteriostatic agents.

Vials of CTLA4Ig drag product for Injection, 250 mg/vial, should be stored under refrigeration (2-8° C.) and protected from long-term exposure to light. Intact vials are stable for at least one year under these conditions. All dilutions of CTLA4Ig drug product for injection must be used within 12 hours after reconstitution of the original vial.

Specific stability guidelines for each dilution are as follows:

Reconstituted CTLA4Ig drug product for Injection, 25 mg/mL, may be stored at temperatures from 15-25° C. and room light or at refrigeration (2-8° C.) for up to 6 hours in the original vial.

Dilutions of reconstituted CTLA4Ig drug product for Injection 10 mg/mL in NS in polyvinyl chloride (PVC) or non-PVC IV bags may be stored at temperatures from 15-25° C. and room light or at refrigeration (2-8° C.) for no more than 12 hours from the time of initial reconstitution.

Diluted solutions of CTLA4Ig drug product for Injection are compatible with standard PVC IV infusion sets.

Results

A planned interim analysis was done after all randomized subjects either completed the Month 12 visit or discontinued prematurely to look at the primary efficacy endpoint to the development of RA. 51/56 randomized patients were evaluable (mean age: 45 yrs; mean duration of symptoms: 7 months [range 1-18 months]; mean CRP level: 1.1 mg/dL); 80% had oligoarthritis, 50% had erosions. By 1 yr, 12/27 (44%) patents treated with CTLA4Ig developed RA vs 16/24 (67%) Pbo-treated patents (23% difference; 95% confidence interval –6 to +48). The time to discontinuation due to development of RA is shown in FIG. 2.

Conclusion

CTLA4Ig retards progression to definite RA in patients with UA. The disease-modifying effects of CTLA4Ig treatment were maintained for 6 months after therapy was stopped.

EXAMPLE IV

The 2 year data for the study described in Example III are presented below. The data includes efficacy, safety, and pharmacodynamic (PD) marker activity data for adults with UA who received up to 6 months of double-blind treatment with CTLA4Ig or placebo. Subjects with persistent UA after 6 months of double-blind study treatment, but who did not meet the criteria for RA, were monitored off study medication for the subsequent development of RA for up to an additional 18 months.

Study Population

A total of 184 subjects were screened, of whom 57 were enrolled and randomized in a 1:1 ratio to double-blind treatment with CTLA4Ig (N=29) or placebo (N=28). Failure to meet the study eligibility criteria was the most frequent reason that subjects were screened but not randomized.

All but 1 of the randomized subjects received at least 1 dose of study medication. One subject assigned to the CTLA4Ig group, was withdrawn due to the presence of erosions detected after randomization but before administration of any study drug. Thus, a total of 56 subjects, 28 in each treatment group, were randomized and received at least 1 dose of study drug.

Among subjects who were randomly assigned to treatment, 39 (22 CTLA4Ig, 17 placebo) completed the 6-month study drug treatment period and entered into the 18-month observation period. Of these, 28 withdrew prematurely before completing the observation period (15 in the CTLA4Ig group, 13 in the placebo group). Sixteen (16) of these 28 subjects (8 in each treatment group) discontinued before Month 12. A total of 7 (25.0%) subjects in the CTLA4Ig group and 4 subjects (14.3%) in the placebo group completed the 24-month study.

Lack of efficacy was the most frequent reasons for premature discontinuation during the study drug treatment period, with more than twice as many subjects in the placebo group (n=8, 28.5%) compared with the CTLA4Ig group (n=3, 10.7%) discontinued for this reason. Lack of efficacy was also the most common reason for withdrawal from the observation period. During this 18-month period the proportion of subjects entering the observation period who were discontinued for this reason was again higher for the placebo group (12/17, 70.6%) than for the CTLA4Ig group (11/22, 50.0%). Among the 23 subjects who were discontinued due to lack of efficacy during the observation period, 14 (7 CTLA4Ig, 7 placebo) were withdrawn before Month 12.

Adverse events led to the premature discontinuation of 1 subject in the CTLA4Ig group during the study drug treatment period and 1 subject in the placebo group during the observation period.

The CTLA4Ig and placebo groups were balanced with respect to demographic characteristics of age, weight, gender distribution, and racial distribution. The mean age of the 56 randomized and treated subjects was 44.8 years (range: 23 to 74 years). Most subjects were White (85.7%) and female (71.4%). While the majority of subjects in both treatment groups were enrolled at sites in Europe (60.7% for CTLA4Ig group, 75.0% for placebo group), a higher percentage of subjects in the CTLA4Ig group were enrolled at sites in South America (17.9% vs 7.1% for placebo group).

The CTLA4Ig and placebo groups were generally balanced with respect to baseline disease characteristics. All but 5 subjects had disease involving at least 2 joints; 2 subjects in each treatment group had disease involving only 1 joint, and one subject in the CTLA4Ig group had no synovitis at screening or baseline (Day 1). This latter subject was enrolled because she met 3 diagnostic criteria for RA (ARA 1987 criteria), but was excluded from the primary efficacy analysis for this relevant protocol deviation. The remaining subjects met between 1 and 3 diagnostic criteria for RA, with the majority of subjects (58.9%) fulfilling 3 criteria. Across all subjects, the mean duration of inflammatory arthritis (IA) was 7.9 months and was somewhat longer in the CTLA4Ig group (8.8 months) than in the placebo group (7.1 months). The mean CRP level was similar in the CTLA4Ig and placebo groups (11.2 mg/L and 10.7 rag/L, respectively), as was the percentage of subjects with radiographic evidence of erosions at baseline (53.5% and 57.1%, respectively).

General medical history findings were consistent with active inflammatory disease and were generally similar for the 2 groups. Most subjects (>75%) in both treatment groups were receiving an antirheumatic medication on Day 1 (78.6% in CTLA4Ig, 89.3% placebo), with NSAIDs being the most common antirheumatic medication used.

Fourteen (14) subjects, including 9 assigned to the CTLA4Ig group and 5 assigned to the placebo group, were receiving an oral or injectable corticosteroid drug on Day 1. For 4 subjects (14.3%) assigned to the CTLA4Ig group and 2 subjects (7.1%) assigned to the placebo group, concomitant treatment on Day 1 consisted of a low oral corticosteroid dose (10 mg/day prednisone equivalent).

Extent of Exposure

Despite the higher premature discontinuation rate from the study drug treatment period in the placebo group, most subjects in the CTLA4Ig and placebo groups (89.3% and 75.0%, respectively) received 6 months of treatment and received the scheduled 8 infusions of study drug (75.0% and 71.4%, respectively). One (1) subject in the CTLA4Ig group (3.6%) and 5 subjects in the placebo group (17.9%) received 3 or fewer infusions of study drug. No subject received more than 8 infusions of study drug or had more than 6 months of study treatment.

Most subjects in the All Treated analysis population did not miss a scheduled infusion of CTLA4Ig (85.7%) or placebo (92.9%) during the study drug treatment period, and no subject in either treatment group missed more than 1 scheduled infusion.

The use of low dose corticosteroids during the study drug treatment period was low and similar for the CTLA4Ig and placebo groups in the ITT analysis population, both in terms of the percentage of subjects using these drugs (n=5, 17.9% in each group) and the mean corticosteroid dose at these time points. The same was true for the observation period, where 5 of the 22 subjects who entered this period in the CTLA4Ig group, and 7 of the 17 subjects in the placebo group, had treatment with low dose corticosteroids.

The number of courses of high dose corticosteroid use during the study drug treatment period for the Intent to Treat (ITT) analysis population was also similar for the 2 groups: 3 courses in the CTLA4Ig group (in 2 subjects) and 4 courses in the placebo group (in 4 subjects). High dose corticosteroid use during the study drug treatment period consisted of intramuscular (IM) or intraarticular (IA) corticosteroids; no subject in either group received an oral corticosteroid dose of $\geq$10 mg/day during the study drug treatment period.

During the 18-month Observation period, the number of courses of high dose corticosteroids was 9 in the CTLA4Ig group and 6 in the placebo group. For 2 subjects in each treatment group, high dose corticosteroids consisted of oral doses 10 mg/day. No subject in either treatment group received more than 2 courses of high dose corticosteroids during the study drug treatment or observation periods.

All subjects in the CTLA4Ig group and most subjects (96.4%) in the placebo group received at least 1 concomitant medication during the study drug observation period. The analgesics, acetaminophen and diclofenac, were the most frequently used concomitant medications, each taken by 7 (25.0%) subjects in the CTLA4Ig group and 9 (32.1%) subjects in the placebo group.

Efficacy Results

Results of this study show that 6 months of treatment with CTLA4Ig retards progression to definite RA in subjects with UA. By Month 12, 12 of 26 subjects (46.2%) with UA in the CTLA4Ig group developed RA compared with 16 of 24 subjects (66.7%) with UA in the placebo group. The 95% CI surrounding the 20.5% treatment group difference in favor of CTLA4Ig for the primary efficacy endpoint was (−47.4, 7.8). The proportion of subjects with UA who developed RA by Month 24 was also lower in the CTLA4Ig group (17/23, 73.9%) compared with the placebo group (21/24, 87.5%), although the magnitude of the treatment difference (−13.6%; 95% CI: −37.6, 10.8) was less than that seen at Month 12.

The efficacy of CTLA4Ig in retarding progression to definite RA appeared more pronounced in the subgroup of subjects who had radiographic evidence of erosions at baseline compared with the subgroup without baseline erosions.

The proportion of subjects with UA who developed RA, according to 1987 ARA criteria, within 1 year of starting study medication, was lower for the CTLA4Ig group (12/26, 46.2%) compared with the placebo group (16/24, 66.7%) (−20.5% difference; 95% CI: −47.4, 7.8).

The prespecified sensitivity analysis of the primary efficacy endpoint which included each of the 55 randomized and treated subjects included in the efficacy ITT analysis population provided similar results favoring CTLA4Ig In the sensitivity analysis, the proportion of subjects with UA who developed RA within 1 year of starting study medication was 42.9% for the CTLA4Ig group (12/28 subjects) compared with 59.3% (16/27 subjects) for the placebo group (−16.4% treatment group difference, 95% CI: −42.3, 11.0).

Fewer subjects with UA who were randomly assigned to 6 months of CTLA4Ig treatment (17/23, 73.9%) developed RA, defined using 1987 ARA criteria, by Month 24 compared with subjects assigned to placebo treatment (21/24, 87.5%). The treatment group difference in developing RA at Month 24 was −13.6% (95% CI: −37.6, 10.8). Although study treatment was not administered after Month 6, subjects and investigators remained blinded to the identity of the study treatment that had been administered through the end of the 18-month observation period (Month 24).

The study shows less structural progression, based on radiographs of the feet and hands, in the CTLA4Ig group compared with the placebo group at Month 12, as reflected by smaller mean changes in erosion and JSN scores. In addition, gadolinium-enhanced MR images of the wrists and hands in a subset of 21 subjects indicated minimal evidence for disease progression in the CTLA4Ig group at the end of the study drug treatment period, while mean changes from baseline at Month 6 in MRI erosion, edema and synovitis scores in the placebo group were indicative of disease worsening. The treatment group difference in MRI scores persisted for 6 months after study treatment had ended.

The presence of synovitis was required at the screening or Day 1 timepoints to be enrolled in the study. The proportion of subjects with UA having persistent symptomatic clinical synovitis at Month 6 was less among subjects treated with CTLA4Ig (4/5, 80%) compared with placebo (12/12, 100%). The difference in the proportion of subjects having persistent symptomatic clinical synovitis between the study groups was −20.0% (95% CI: −71.5, 15.21). At Month 12, the proportion of subjects with persistent clinical synovitis was 10 of 11 subjects for the CTLA4Ig group and 7 of 7 subjects for the placebo group.

A total of 11 subjects in the CTLA4Ig group and 10 in the placebo group had gadolinium-enhanced MRI assessments of the hands and wrists; by protocol design, Mills were only performed for subjects enrolled at investigational sites in Europe. Mean changes from baseline in MRI bone erosion and synovitis scores of the hands and wrists at the end of the study drug treatment period (Month 6) indicated minimal disease progression in the CTLA4Ig group (mean changes of 0.45 and 0.27, respectively), while changes were larger and indicative of disease worsening in the placebo group (mean changes of 1.20 and 1.60, respectively). Mean changes from baseline in MRI edema scores at Month 6 indicated an improvement with CTLA4Ig (mean change of −1.64) but worsening with placebo (mean change of 1.40).

A similar pattern of results with respect to MRI scores were seen at Month 12, where 9 and 6 subjects in the CTLA4Ig and placebo groups, respectively, had a MRI performed both at baseline and after 1 year in the study. At Month 12, little change in MRI bone erosion, edema, and synovitis scores were seen relative to baseline values in the CTLA4Ig group (mean changes of 0.0, 0.22, and 0.22, respectively), while continued disease progression was apparent in the placebo group (mean changes of 5.00, 6.67, and 2.33, respectively).

Only 7 subjects (5 CTLA4Ig, 2 placebo) had MRI assessments at baseline and Month 24. In this small subset of European subjects who had not progressed to RA and thus remained in this study, mean baseline MRI scores were small (typically <1.0), and showed little change at Month 24

At the end of the study drug treatment period (Month 6), subjects with UA in the CTLA4Ig group had reductions in disease activity (DAS 28 [CRP] scores) and improvements in physical function (HAQ-DI scores) and health-related quality of life (PCS and MCS scores of SF-36) relative to baseline, while mean scores on these efficacy variables were unchanged in the placebo group. Treatment group differences were smaller at Months 12 and 24 of the untreated observation period.

At the end of the study drug treatment period, disease activity, as assessed using the DAS 28 (CRP) score, was reduced relative to baseline in the CTLA4Ig group (mean change, −1.13) but was unchanged in the placebo group (mean change, 0.01). At Month 6, a clinically significant improvement (reduced at least by a value of 1.2 from baseline in the DAS 28 score) was observed in 8 of the 20 subjects (40%) with baseline and Month 6 scores in the CTLA4Ig group compared with 4 of the 20 subjects (20%) with baseline and Month 6 scores in the placebo group. Consistent with these findings, higher rates of low disease activity (DAS 28 score ≦3.2) or disease remission (DAS 28 score <2.6) at Month 6 were seen in the CTLA4Ig group (81.0% and 71.4%, respectively) compared with the placebo group (45.0% and 35.0%, respectively).

Evaluations of DAS 28 (CRP) data at Months 12 and 24 continued to show larger improvements in disease activity for the CTLA4Ig group compared with the placebo group, but the treatment group differences were smaller during the untreated observation period. Among the 18 subjects in the CTLA4Ig group with baseline and Month 12 DAS 28 scores, the mean change score was −0.50 at Month 12 and about two-thirds (68.4%) of subjects had low disease activity. Among the 13 subjects in the placebo group with DAS 28 data at both time points, there was virtually no change in disease activity at Month 12 compared to baseline (mean change, −0.05), and 53.9% of subjects had low disease activity. Of the 11 subjects who had DAS 28 scores at Month 24, disease remission was seen in 4 of the 7 CTLA4Ig subjects and 2 of the 4 placebo subjects.

During the study drug treatment period, greater improvements in disease activity, as reflected by larger mean changes from baseline and percentage of subjects with improvement, were apparent for the CTLA4Ig group compared with the placebo group as early as Day 29.

The proportion of subjects with a clinically meaningful improvement in physical function (defined as ≧0.3 reduction from baseline in HAQ-DI score) was larger for the CTLA4Ig group than for the placebo group at Months 6, 12, and 24. At the end of the study drug treatment period, 61.5% of randomized and treated subjects in the CTLA4Ig group compared with 24.0% of those in the placebo group had a clinically meaningful improvement in HAQ-DI (treatment group difference of 37.5% [95% CI: 9.9, 61.4]). The proportion of subjects in the CTLA4Ig group who had at a clinically meaningful improvement following 6 and 12 months of untreated follow-up (36.0% at Month 12 and 14.3% at Month 24) was less than that seen after 6 months of treatment, but nevertheless was still numerically greater than the proportions with a clinically meaningful improvement in the placebo group at Months 12 and 24 (12.0% and 4.2%, respectively).

Larger mean improvements from baseline in the physical and mental component summary measures of the SF-36 were observed for the CTLA4Ig group at Months 6, 12, and 24 compared with the placebo group. The mean improvement from baseline at the end of the study drug treatment period (Month 6) was 10.23 for the PCS score and 2.54 for the MCS score in the CTLA4Ig group. Mean changes in the physical component summary (PCS) and mental component summary (MCS) scores at Month 6 in the placebo group were small (1.95 and −0.30, respectively).

Among subjects in the CTLA4Ig group who remained in the study during the untreated observation period, the mean improvements at Months 12 and 24 were 3.83 and 2.46, respectively, for the PCS score and 2.50 and 3.75, respectively, for the MCS score. In the placebo group, PCS and MCS scores worsened during the 18-month untreated observation period, as reflected by mean negative mean change from baseline values at Months 12 and 24 for these endpoints.

Baseline radiographic scores indicated minimal bone erosion or joint space narrowing among randomized subjects, consistent with the study eligibility criteria that subjects not have a diagnosis of RA at study entry. During the 6-month study drug treatment period, there was little change in radiographic Erosion, JSN, or Total scores relative to baseline, as reflected by mean change scores at Month 6 for all 3 endpoints of $\leq 0.13$ in the CTLA4Ig and of $\leq 0.47$ in the placebo group. There was a suggestion of less structural progression in the CTLA4Ig group compared with the placebo group at Month 12, where the mean change in the Total score was 0.02 in the CTLA4Ig group and 1.11 in the placebo group.

Results of imputed radiographic erosion and JSN scores analysis showed smaller mean changes, indicative of lesser structural progression, after 6 and 12 months after the end of the study drug treatment period (i.e., Months 12 and 24) in the CTLA4Ig group (mean change in Total scores of 0.29 and 0.02) compared with the placebo group (1.21 and 2.13).

Subjects in the CTLA4Ig group showed mean percent improvements in the individual ACR components during the study drug treatment period. At Month 6, the mean percent improvements in assessments of tender joints, swollen joints, and subject-rated pain were 64.91%, 57.34%, and 70.03%, respectively. By comparison, subjects in the placebo group showed a worsening in ACR individual core components during the study drug treatment period, with mean percent changes in ratings of tender joints, swollen joints, and subject-rated pain of −63.3%, −10.5%, and −83.4%, respectively.

The mean percent improvements in the ACR components seen for the CTLA4Ig group during the study drug treatment period were not maintained once study treatment was stopped among subjects who remained in the study.

The primary and related secondary efficacy endpoints, as well as demographic and baseline disease characteristics, were examined separately for subgroups defined based on the presence or absence of erosions at study entry (i.e., randomization strata).

Demographic characteristics were similar among the subset of 31 subjects with radiographic evidence of erosion at baseline and the subset of 25 subjects without radiographic evidence of erosion at baseline. Baseline disease characteristics were also similar for these 2 subgroups, except that the mean and median radiographic erosion score was higher for the subgroup with baseline erosions than in the subgroup without baseline erosions.

Among the subgroup of subjects with radiographic evidence of erosion at baseline, the proportion of subjects with UA who developed RA, according to 1987 ARA criteria, within 1 year of starting study medication, was lower for the CTLA4Ig group (4/13, 30.8%) than for the placebo group (9/14, 64.3%). Among the subgroup of subjects without radiographic evidence of erosions at baseline, 61.5% of subjects in the CTLA4Ig group (8/13) and 70.0% of subjects in the placebo group (7/10) developing RA by Month 12.

The proportion of subjects with UA who developed RA by Month 24 was lower for the CTLA4Ig group than for the placebo group only among subjects who had radiographic evidence of erosions at baseline (50.0% [6/12 subjects] for CTLA4Ig; 85.7% [12/14 subjects] for placebo). Among the subgroup of subjects who had no radiographic evidence of erosions at baseline, 100% of subjects in the CTLA4Ig group (11/11) and 90% of subjects in the placebo group (9/10) had developed RA by Month 24.

Safety

CTLA4Ig, administered IV monthly at a weight-tiered dose of 10 mg/kg for up to 6 months, was generally well tolerated in the treatment of adults with UA. No deaths were reported during the study. During the study drug treatment period, SAEs were reported for 1 subject in the CTLA4Ig group (basal cell carcinoma) and 1 subject in the placebo group (sciatica). Both SAEs were assessed by the investigator as unrelated to study treatment. One (1) subject each in the CTLA4Ig and placebo groups was discontinued from treatment during the study drug treatment period due to an AE. Acute infusional AEs (reported within 1 hour of the start of study drug infusion) were reported for 1 subject in each treatment group; the acute infusional AE in the CTLA4Ig group (dyspnea) occurred during the first infusion and resulted in treatment discontinuation. Infections or infestations were reported during the study drug treatment period in a similar percentage of subjects in the CTLA4Ig (35.7%) and placebo (39.3%) groups. None of the reported infections in the CTLA4Ig group were severe in intensity. During the study drug treatment period, AEs were reported for a similar percentage of subjects in the CTLA4Ig (64.3%) and placebo (71.4%) groups. All AEs in the CTLA4Ig group were mild or moderate in intensity. No safety issues emerged from the evaluation of laboratory or vital sign data.

Overall, AEs were reported for 18 (64.3%) subjects treated with CTLA4Ig and 20 (71.4%) subjects treated with placebo during the study drug treatment period or within 56 days of the last infusion of study medication. The frequencies of adverse events were generally similar for the CTLA4Ig and placebo groups. The most frequently reported AEs by system organ class (SOC) were infections and infestations (35.7% CTLA4Ig; 39.3% placebo), gastrointestinal (21.4% CTLA4Ig; 25.0% placebo), and respiratory, thoracic and mediastinal disorders (17.9% CTLA4Ig; 21.4% placebo). Adverse events reported by at least 10% of subjects in either treatment group during the study treatment period were diarrhea (14.3% CTLA4Ig; 10.7% placebo), headache (10.7% CTLA4Ig; 7.1% placebo), nasopharyngitis (10.7% CTLA4Ig; 7.1% placebo), urinary tract infection (7.1% CTLA4Ig; 10.7% placebo), pharyngolaryngeal pain (3.6% CTLA4Ig; 14.3% placebo), and gastroenteritis (0% CTLA4Ig; 10.7% placebo). No autoimmune disorders were reported during the study treatment period in either treatment group.

The proportion of subjects in the placebo group with AEs of severe intensity was 10.7% (single severe AEs of sciatica, viral infection, pharyngeal oedema). No subject in the CTLA4Ig group had an AE during the study drug treatment period that was considered of severe or very severe in intensity according to the investigator.

The frequency of related AEs was 50% (n=14) for the CTLA4Ig group and 35.7% (n=10) for the placebo group during the study drug treatment period. The most common individual related AE was headache, reported for 3 subjects (10.7%) in the CTLA4Ig group and 2 subjects (7.1%) for the placebo group. Eczema was the only other related AE reported by >1 CTLA4Ig-treated subject, and was reported for 2 subjects (7.1%).

The clinical laboratory data were generally unremarkable, and no safety issues were identified in this population with UA.

During the study drug treatment period, the frequency of hematologic and blood chemistry parameters that met the sponsor-defined marked abnormality (MA) criteria was small and similar in the CTLA4Ig and placebo groups. For each hematology and blood chemistry parameter, MAs were identified for 2 or fewer subjects in either treatment group.

Small changes from baseline (Day 1) in hematologic and blood chemistry parameters were noted during the study drug treatment and observation periods, and these changes showed considerable variation and no consistent pattern across 2 groups.

Additionally, blood neutrophils, ALT, and AST levels remained stable following treatment with CTLA4Ig during the entire study period. No subject in either treatment group had an ALT or AST value that was >3×ULN (upper limit of normal) at any measurement time point, or a neutrophil count value that was <0.5×109 cells/L or >15×109 cells/L.

Two subjects had laboratory abnormalities reported as an AE during the study drug treatment period. Increased hepatic enzymes were reported as an AE in a subject in the CTLA4Ig group on Day 141, and persisted for 120 days before resolving, No hepatic enzyme values in this subject met the MA criteria. Thrombocytopenia was reported as an AE in one subject in the placebo group and led to the discontinuation of study treatment. Platelet count values for this subject were $284 \times 10^{-9}$ c/L at baseline and declined steadily during the study, and were $86 \times 10^{-9}$ c/L at Day 169 and $22 \times 10^{-9}$ c/L at the last recorded value on Day 319.

Mean values for all vital sign parameters remained stable throughout the study drug treatment period in the CTLA4Ig and placebo groups.

Most subjects in both treatment groups had a normal ECG at baseline and again at the end of the study drug treatment period. The proportion of subjects whose ECG was normal at baseline but abnormal at Day 169 (or at time of early termination) was similar for the CTLA4Ig (1/24, 4.2%) and placebo (2/23, 8.7%) groups.

Pharmacodynamic Results

Treatment with CTLA4Ig was associated with mean reductions from baseline at Month 6 in IL-6 (−4.49 pg/mL), TFN-α(−1.70 pg/mL), IL-1β (−0.12 pg/mL), and MMP-3 (−2.29 ng/mL). By comparison, small mean increases or no change relative to baseline was seen in the placebo group at Month 6 for IL-6 (1.08 pg/mL), TFN-α (0.07 pg/mL), IL-1β (−0.09 pg/mL), and MMP-3 (14.34 ng/mL).

After 6 months with no study treatment, the CTLA4Ig group still had larger mean decreases for most of these cytokines compared to the placebo group. At Month 12, mean changes from baseline for the CTLA4Ig and placebo groups were −0.14 and 6.37 pg/mL, respectively, for IL-6; −0.50 and −0.10 pg/mL, respectively, for TFN-α; and −2.55 and 25.34 ng/mL, respectively, for MMP-3. No difference was seen between the 2 groups in the mean change from baseline for IL-1β at Month 12 (−0.09 and −0.24 pg/mL); however, the number of subjects with baseline and Month 12 data was small (n=7 in placebo group and n=13 in CTLA4Ig group).

Only 5 subjects in the CTLA4Ig group and 3 in the placebo group had baseline and Month 24 cytokine data. A mean decrease in IL-6 and TFN-α was still apparent in this small subset of CTLA4Ig-treated subjects who had not developed RA (−3.44 pg/mL and −0.82 pg/mL, respectively).

All subjects were positive for anti-CCP2 antibodies on Day 1, consistent with study eligibility criteria. In the placebo group, all subjects with evaluable data remained positive at Months 6, 12, and 24. By comparison, the percentage of subjects with UA who were positive for anti-CCP2 antibodies declined in the CTLA4Ig group to 90.9% (20/22 subjects) at Month 6, 86.7% (13/15 subjects) at Month 12, and 83.3% (5/6 subjects) at Month 24.

These data are consistent with results for serum levels of anti-CCP2 antibodies. In the CTLA4Ig group, mean reductions from baseline were seen in anti-CCP2 antibodies at Month 6 (−94.5 U/L) and Month 12 (−6.46 U/L). In the placebo group, levels of anti-CCP2 antibodies were increased relative to baseline values at Month 6 (mean change, 16.32 U/L) and Month 12 (149.5 U/L). Only 6 subjects in the CTLA4Ig group and 3 in the placebo group had baseline and Month 24 anti-CCP2 data. One (1) of these CTLA4Ig subjects was negative for anti-CCP2 antibodies.

At baseline (Day 1), 85.7% of subjects in the CTLA4Ig group and 71.4% of subjects in the placebo group were. RF positive. In the CTLA4Ig group, this percentage declined to 59.1% at the end of the study drug treatment period (Month 6). After 6 and 18 months of untreated follow-up, the proportion of subjects remaining in the study who were RF positive was 11 of 15 (73.3%) at Month 12 and 3 of 6 (50.0%) at Month 24. By comparison, the proportion of subjects in the placebo group who were RF positive increased over the 24-month study (14 of 20 [70.0%] at Month 6 to 3 of 3 [100%] at Month 24).

No subject in the CTLA4Ig group had a positive RF seroconversion at Month 6, 12, or 24. In the placebo group, 2 of the 7 evaluated subjects who were RF negative at baseline were positive at Month 6, and 1 of the 2 evaluable subjects who were RF negative at baseline was positive at Month 12.

At baseline (Day 1), the percentage of subjects for whom the shared epitope allele HLA-DRB10401, HLA-DRB10404, and HLA-DRB10101 was detected was similar for the CTLA4Ig (46.4% [13/28]) and placebo (39.3% [11/28]) groups.

Immunogenicity

Immunogenicity data were available from a total of 23 of the 28 randomized and treated subjects in the CTLA4Ig group. No subject was seropositive for anti-CTLA4Ig antibodies (specific for the IgG portion of the molecule) at any time during the 24-month study period.

Four (4) of the 23 subjects (17.4%) were seropositive in the anti-CTLA4-T assay (Tip). In these 4 subjects, anti-CTLA4-T antibodies were not detected at 3 months after last dose (Month 9 sample) but were detected 6 months after last dose (Month 12 sample). The titers in these subjects were low (range: 65 to 98; assay sensitivity is 25). Of these 4 samples, 2 contained neutralizing antibodies and 2 did not.

The presence of a positive antibody seroconversion response did not appear to affect safety. No AEs were reported in the subject or in temporal proximity to the positive seroconversion response in subjects. In one subject, tenosynovitis was reported with an onset on Day 384, approximately 6 months after the last dose of study drug (CTLA4Ig) and near the time of the positive seroconversion response. This AE was assessed as unlikely related to study treatment and moderate in intensity, and was reported to persist.

OVERALL CONCLUSIONS

Results for the primary and related key secondary efficacy endpoints in this study suggest that CTLA4Ig, administered as monotherapy for 6 months at a weight-tiered dose of 10 mg/kg IV, retards progression to definite RA in subjects with UA, and the disease-modifying effects of CTLA4Ig were observed 6 and 18 months after the drug was stopped. In subjects with UA, larger improvements in physical function, physician-reported disease activity, and health-related quality of life were seen following 6 months of treatment with CTLA4Ig than with placebo. Radiographic evaluations of the hands and feet indicated minimal disease progression during the study drug treatment period among subjects receiving CTLA4Ig; the progression of structural damage was also less 6 months after the drug was stopped in the CTLA4Ig group than in the placebo group. MRI evaluations of the wrists and hands were more limited but showed a similar trend. Compared with placebo, treatment with CTLA4Ig was associated with a larger reduction in serum levels of anti-CCP2 antibodies and a decrease in the percentage of subjects who were positive for anti-CCP2 antibodies and RF. CTLA4Ig at a weight-tiered dose of 10 mg/kg administered IV monthly for 6 months was well tolerated by subjects with UA. The immunogenicity rate (drug-induced positive seroconversion) was low, and the presence of antibodies to CTLA4Ig or CTLA4-T did not correlate with any clinical safety findings in this exploratory study

What is claimed is:

1. A method for retarding progression to definite rheumatoid arthritis in subjects with undifferentiated arthritis who are at high risk for the development of rheumatoid arthritis comprising administering to the subject a CTLA4 molecule, wherein the CTLA4 molecule binds CD80 and/or CD86 and comprises an extracellular domain of CTLA4 as shown in SEQ ID NO:2 beginning with alanine at position 26 or methionine at position 27 and ending with aspartic acid at position 150.

2. The method of claim 1 further comprising an amino acid sequence which alters the solubility or affinity of the CTLA4 molecule.

3. The method of claim 2, wherein the amino acid sequence which alters the solubility or affinity comprises an immunoglobulin.

4. The method of claim 3, wherein the immunoglobulin is an immunoglobulin constant region or portion thereof.

5. The method of claim 4, wherein the immunoglobulin constant region or portion thereof is mutated to reduce effector function.

6. The method of claim 4, wherein the immunoglobulin constant region or portion thereof comprises a hinge, CH2 and CH3 regions of a human or monkey immunoglobulin molecule.

7. The method of claim 5, wherein the immunoglobulin constant region or portion thereof comprises a hinge, CH2 and CH3 regions of a human or monkey immunoglobulin molecule.

8. A method for retarding progression to definite rheumatoid arthritis in subjects with undifferentiated arthritis who are at high risk for the development of rheumatoid arthritis comprising administering to the subject a CTLA4 molecule, wherein the CTLA4 molecule comprises:
   (a) an amino acid sequence beginning with methionine at position 27 and ending with lysine at position 383 of SEQ ID NO:2, or
   (b) an amino acid sequence beginning with alanine at position 26 and ending with lysine at position 383 of SEQ ID NO:2.

9. A method for retarding progression to definite rheumatoid arthritis in subjects with undifferentiated arthritis who are at high risk for the development of rheumatoid arthritis comprising administering to the subject a CTLA4 molecule encoded by the nucleic acid molecule designated ATCC® No. 68629.

10. A method for improving physical function of subjects with undifferentiated arthritis comprising administering to the subject a CTLA4 molecule, wherein the CTLA4 molecule binds CD80 and/or CD86 and comprises an extracellular domain of CTLA4 as shown in SEQ ID NO:2 beginning with alanine at position 26 or methionine at position 27 and ending with aspartic acid at position 150.

11. The method of claim 10, wherein the improved physical function is measured by Health Assessment Questionnaire Disability Index (HAQ-DI).

12. The method of any one of claims 1 to 10, wherein the CTLA4 molecule is administered in an amount of 10 mg/kg weight of the subject.

* * * * *

SEQUENCE LISTING

```
<160> NUMBER OF SEQ ID NOS: 2

<210> SEQ ID NO 1
<211> LENGTH: 1223
<212> TYPE: DNA
<213> ORGANISM: Homo sapiens
<220> FEATURE:
<221> NAME/KEY: CDS
<222> LOCATION: (11)..(1159)

<400> SEQUENCE: 1
agcttcacca atg ggt gta ctg ctc aca cag agg acg ctg ctc agt ctg         49
            Met Gly Val Leu Leu Thr Gln Arg Thr Leu Leu Ser Leu
            1               5                   10 gtc ctt gca ctc ctg ttt cca agc atg gcg agc atg gca atg cac gtg       97
Val Leu Ala Leu Leu Phe Pro Ser Met Ala Ser Met Ala Met His Val
    15                  20                  25 gcc cag cct gct gtg gta ctg gcc agc agc cga ggc atc gcc agc ttt      145
Ala Gln Pro Ala Val Val Leu Ala Ser Ser Arg Gly Ile Ala Ser Phe
30                  35                  40                  45 gtg tgt gag tat gca tct cca ggc aaa gcc act gag gtc cgg gtg aca      193
Val Cys Glu Tyr Ala Ser Pro Gly Lys Ala Thr Glu Val Arg Val Thr
                50                  55                  60 gtg ctt cgg cag gct gac agc cag gtg act gaa gtc tgt gcg gca acc      241
Val Leu Arg Gln Ala Asp Ser Gln Val Thr Glu Val Cys Ala Ala Thr
            65                  70                  75 tac atg atg ggg aat gag ttg acc ttc cta gat gat tcc atc tgc acg      289
Tyr Met Met Gly Asn Glu Leu Thr Phe Leu Asp Asp Ser Ile Cys Thr
        80                  85                  90 ggc acc tcc agt gga aat caa gtg aac ctc act atc caa gga ctg agg      337
Gly Thr Ser Ser Gly Asn Gln Val Asn Leu Thr Ile Gln Gly Leu Arg
    95                  100                 105 gcc atg gac acg gga ctc tac atc tgc aag gtg gag ctc atg tac cca      385
Ala Met Asp Thr Gly Leu Tyr Ile Cys Lys Val Glu Leu Met Tyr Pro
110                 115                 120                 125 ccg cca tac tac ctg ggc ata ggc aac gga acc cag att tat gta att      433
Pro Pro Tyr Tyr Leu Gly Ile Gly Asn Gly Thr Gln Ile Tyr Val Ile
                130                 135                 140 gat cca gaa ccg tgc cca gat tct gat cag gag ccc aaa tct tct gac      481
Asp Pro Glu Pro Cys Pro Asp Ser Asp Gln Glu Pro Lys Ser Ser Asp
            145                 150                 155 aaa act cac aca tcc cca ccg tcc cca gca cct gaa ctc ctg ggg gga      529
Lys Thr His Thr Ser Pro Pro Ser Pro Ala Pro Glu Leu Leu Gly Gly
        160                 165                 170 tcg tca gtc ttc ctc ttc ccc cca aaa ccc aag gac acc ctc atg atc      577
Ser Ser Val Phe Leu Phe Pro Pro Lys Pro Lys Asp Thr Leu Met Ile
    175                 180                 185 tcc cgg acc cct gag gtc aca tgc gtg gtg gtg gac gtg agc cac gaa      625
```

```
                                                                              -continued Ser Arg Thr Pro Glu Val Thr Cys Val Val Asp Val Ser His Glu
190                 195                 200                 205 gac cct gag gtc aag ttc aac tgg tac gtg gac ggc gtg gag gtg cat          673
Asp Pro Glu Val Lys Phe Asn Trp Tyr Val Asp Gly Val Glu Val His
        210                 215                 220 aat gcc aag aca aag ccg cgg gag gag cag tac aac agc acg tac cgt          721
Asn Ala Lys Thr Lys Pro Arg Glu Glu Gln Tyr Asn Ser Thr Tyr Arg
                225                 230                 235 gtg gtc agc gtc ctc acc gtc ctg cac cag gac tgg ctg aat ggc aag          769
Val Val Ser Val Leu Thr Val Leu His Gln Asp Trp Leu Asn Gly Lys
        240                 245                 250 gag tac aag tgc aag gtc tcc aac aaa gcc ctc cca gcc ccc atc gag          817
Glu Tyr Lys Cys Lys Val Ser Asn Lys Ala Leu Pro Ala Pro Ile Glu
    255                 260                 265 aaa acc atc tcc aaa gcc aaa ggg cag ccc cga gaa cca cag gtg tac          865
Lys Thr Ile Ser Lys Ala Lys Gly Gln Pro Arg Glu Pro Gln Val Tyr
270                 275                 280                 285 acc ctg ccc cca tcc cgg gat gag ctg acc aag aac cag gtc agc ctg          913
Thr Leu Pro Pro Ser Arg Asp Glu Leu Thr Lys Asn Gln Val Ser Leu
                290                 295                 300 acc tgc ctg gtc aaa ggc ttc tat ccc agc gac atc gcc gtg gag tgg          961
Thr Cys Leu Val Lys Gly Phe Tyr Pro Ser Asp Ile Ala Val Glu Trp
        305                 310                 315 gag agc aat ggg cag ccg gag aac aac tac aag acc acg cct ccc gtg         1009
Glu Ser Asn Gly Gln Pro Glu Asn Asn Tyr Lys Thr Thr Pro Pro Val
                320                 325                 330 ctg gac tcc gac ggc tcc ttc ttc ctc tac agc aag ctc acc gtg gac         1057
Leu Asp Ser Asp Gly Ser Phe Phe Leu Tyr Ser Lys Leu Thr Val Asp
    335                 340                 345 aag agc agg tgg cag cag ggg aac gtc ttc tca tgc tcc gtg atg cat         1105
Lys Ser Arg Trp Gln Gln Gly Asn Val Phe Ser Cys Ser Val Met His
350                 355                 360                 365 gag gct ctg cac aac cac tac acg cag aag agc ctc tcc ctg tct ccg         1153
Glu Ala Leu His Asn His Tyr Thr Gln Lys Ser Leu Ser Leu Ser Pro
                370                 375                 380 ggt aaa tgagtgcgac ggccggcaag ccccgctccc cgggctctcg cggtcgcacg          1209
Gly Lys aggatgcttc taga                                                         1223

<210> SEQ ID NO 2
<211> LENGTH: 383
<212> TYPE: PRT
<213> ORGANISM: Homo sapiens

<400> SEQUENCE: 2

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110
```

-continued

```
Thr Gly Leu Tyr Ile Cys Lys Val Glu Leu Met Tyr Pro Pro Pro Tyr
            115                 120                 125
Tyr Leu Gly Ile Gly Asn Gly Thr Gln Ile Tyr Val Ile Asp Pro Glu
        130             135                 140
Pro Cys Pro Asp Ser Asp Gln Glu Pro Lys Ser Ser Asp Lys Thr His
145             150                 155                     160
Thr Ser Pro Pro Ser Pro Ala Pro Glu Leu Leu Gly Gly Ser Ser Val
            165                 170                 175
Phe Leu Phe Pro Pro Lys Pro Lys Asp Thr Leu Met Ile Ser Arg Thr
            180             185                 190
Pro Glu Val Thr Cys Val Val Val Asp Val Ser His Glu Asp Pro Glu
        195             200                 205
Val Lys Phe Asn Trp Tyr Val Asp Gly Val Glu Val His Asn Ala Lys
    210                 215                 220
Thr Lys Pro Arg Glu Glu Gln Tyr Asn Ser Thr Tyr Arg Val Val Ser
225             230             235                     240
Val Leu Thr Val Leu His Gln Asp Trp Leu Asn Gly Lys Glu Tyr Lys
                245                 250                 255
Cys Lys Val Ser Asn Lys Ala Leu Pro Ala Pro Ile Glu Lys Thr Ile
            260                 265                 270
Ser Lys Ala Lys Gly Gln Pro Arg Glu Pro Gln Val Tyr Thr Leu Pro
        275                 280                 285
Pro Ser Arg Asp Glu Leu Thr Lys Asn Gln Val Ser Leu Thr Cys Leu
    290                 295                 300
Val Lys Gly Phe Tyr Pro Ser Asp Ile Ala Val Glu Trp Glu Ser Asn
305             310                 315                     320
Gly Gln Pro Glu Asn Asn Tyr Lys Thr Thr Pro Pro Val Leu Asp Ser
                325                 330                 335
Asp Gly Ser Phe Phe Leu Tyr Ser Lys Leu Thr Val Asp Lys Ser Arg
            340                 345                 350
Trp Gln Gln Gly Asn Val Phe Ser Cys Ser Val Met His Glu Ala Leu
        355                 360                 365
His Asn His Tyr Thr Gln Lys Ser Leu Ser Leu Ser Pro Gly Lys
    370                 375                 380
```